(12) United States Patent
Schwarz et al.

(10) Patent No.: US 9,487,577 B2
(45) Date of Patent: Nov. 8, 2016

(54) **ANTI-GLUCOSAMINIDASE PASSIVE IMMUNIZATION FOR *STAPHYLOCOCCUS AUREUS* INFECTIONS**

(71) Applicant: UNIVERSITY OF ROCHESTER, Rochester, NY (US)

(72) Inventors: Edward M. Schwarz, Rochester, NY (US); Mark A. Sullivan, Fairport, NY (US); John L. Daiss, Rochester, NY (US)

(73) Assignee: University of Rochester, Rochester, NY (US)

(*) Notice: Subject to any disclaimer, the term of this patent is extended or adjusted under 35 U.S.C. 154(b) by 255 days.

(21) Appl. No.: 14/355,524

(22) PCT Filed: Oct. 30, 2012

(86) PCT No.: PCT/US2012/062589
§ 371 (c)(1),
(2) Date: Apr. 30, 2014

(87) PCT Pub. No.: WO2013/066876
PCT Pub. Date: May 10, 2013

(65) Prior Publication Data
US 2014/0371428 A1    Dec. 18, 2014

Related U.S. Application Data

(60) Provisional application No. 61/554,777, filed on Nov. 2, 2011.

(51) Int. Cl.
*C07K 19/00* (2006.01)
*C07K 16/12* (2006.01)
*A61K 39/00* (2006.01)

(52) U.S. Cl.
CPC ..... *C07K 16/1271* (2013.01); *A61K 2039/505* (2013.01); *C07K 2317/24* (2013.01); *C07K 2317/56* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 2002/0076766 A1 | 6/2002 | Black et al. | |
| 2010/0136009 A1 | 6/2010 | Papkoff et al. | |
| 2011/0076284 A1 | 3/2011 | Corbin et al. | |

FOREIGN PATENT DOCUMENTS

WO    2011140114 A2    11/2011

OTHER PUBLICATIONS

Vajdos et al. (J Mol Biol. Jul. 5, 2002;320(2):415-28.*
Brown et al. (J Immunol. May 1996;156(9):3285-91.*
Varrone et al., "Evaluation of Anti-Glucosaminidase Monoclonal Antibodies as a Passive Immunization for Methicillin-Resistant *Staphylococcus aureus* (MRSA) Osteomyelitis," 57th Annu Meet Orthop Res Soc (ORS), Long Beach, CA (Jan. 13-16, 2011).
Baba et al., "Targeting of Muralytic Enzymes to the Cell Division Site of Gram-positive Bacteria: Repeat Domains Direct Autolysin to the Equatorial Surface Ring of *Staphylococcus aureus*," The EMBO Journal 17(16):4639-4646 (1998).
European Search Report for EP 12845928.6 dated Oct. 29, 2014.
Guardati et al., "The Use of Monoclonal Antibodies for Studying the Biological Properties of *Staphylococcus aureus* Endo-γ-N-acetylglucosaminidase," FEMS Microbiol. Let. 112:73-80 (1993).
Sugai et al., "Localized Perforation of the Cell Wall by a Major Autolysin: atl Gene Products and the Onset of Penicillin-Induced Lysis of *Staphylococcus aureus*," J. Bacteriol. 179(9):2958-2962 (1997).
Francis et al., "Monitoring Bioluminescent *Staphylococcus aureus* Infections in Living Mice Using a Novel luxABCDE Construct," Infect. Immun. 68(6):3594-3600 (2000).
Office Action for Canadian Application No. 2,853,943 dated Jul. 16, 2014.
Office Action for Japanese Application No. 2014-540015 dated Oct. 15, 2014 (translation only).
Office Action for Australian Application No. 2012332777 dated Jul. 9, 2014.
Varrone et al., "Anti-glucosaminidase Monoclonal Antibodies as a Passive Immunization for Methicillin-Resistant *Staphylococcus aureus* (MRSA) Orthopedic Infections", IBMS BoneKEy 8(4):187-194 (2011).
International search report and written opinion for corresponding application No. PCT/US12/062589, mailed Mar. 14, 2013.

* cited by examiner

*Primary Examiner* — Brian J Gangle
(74) *Attorney, Agent, or Firm* — LeClairRyan, a Professional Corporation

(57) ABSTRACT

The present invention is directed to a monoclonal antibody that binds specifically to a *Staphylococcus aureus* glucosaminidase and inhibits in vivo growth of *S. aureus*. Also disclosed are monoclonal antibody binding portions, recombinant or hybridoma cell lines, pharmaceutical compositions containing the monoclonal antibody or binding portions thereof, and methods of treating *S. aureus* infection and osteomyelitis, and methods for introducing an orthopedic implant into a patient using the monoclonal antibody, binding portion, or pharmaceutical composition of the present invention.

11 Claims, 12 Drawing Sheets

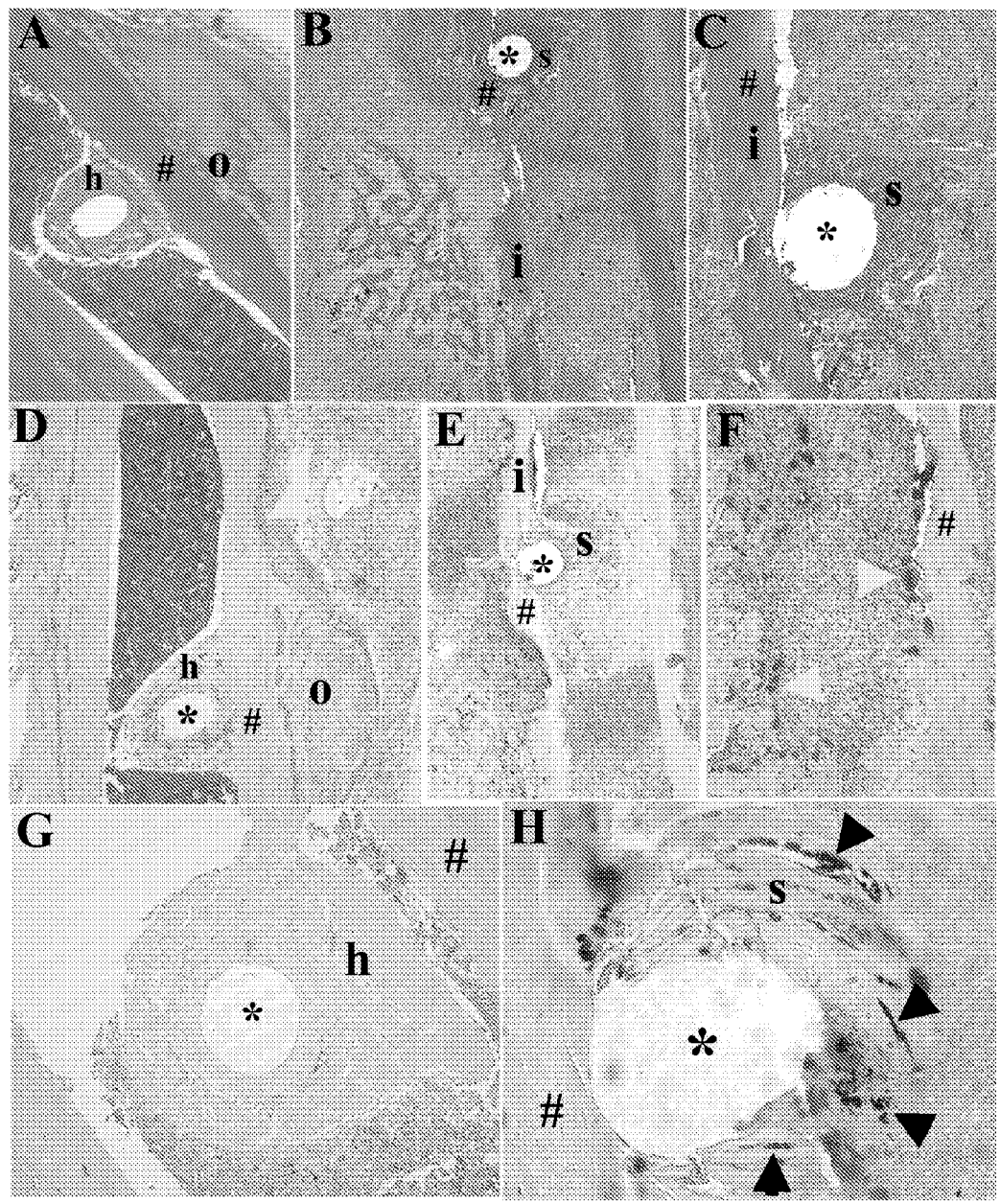
FIGS. 2A-H

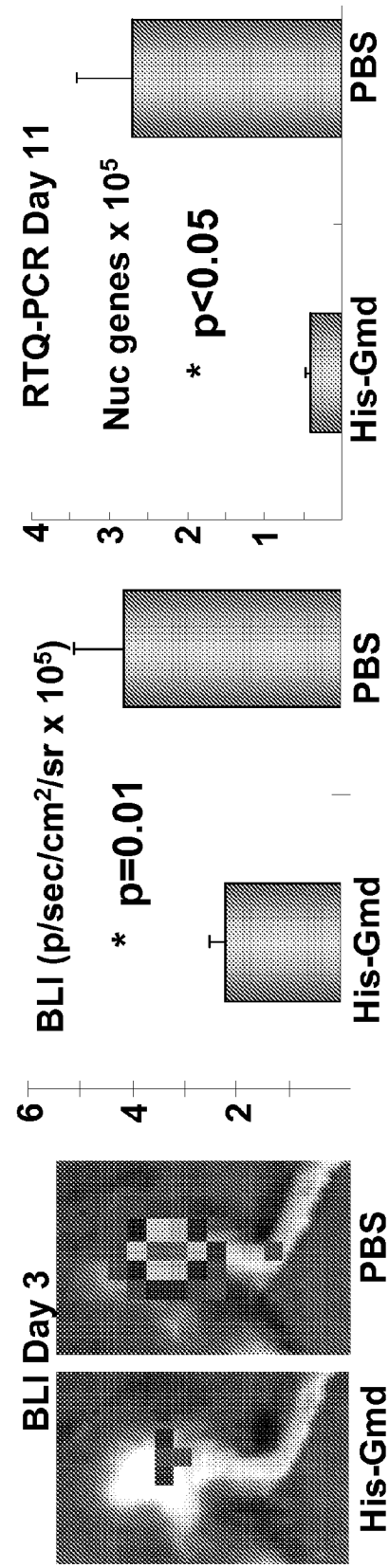

FIG 11A
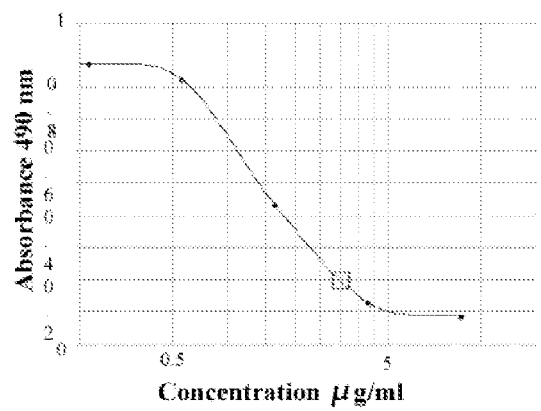
FIG. 11B
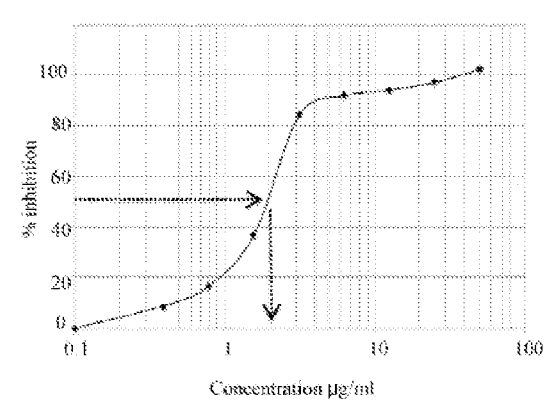
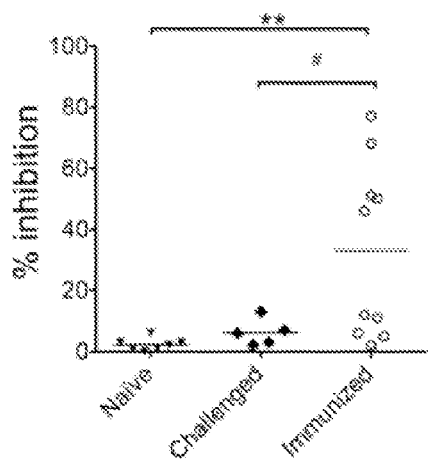
FIG 11C
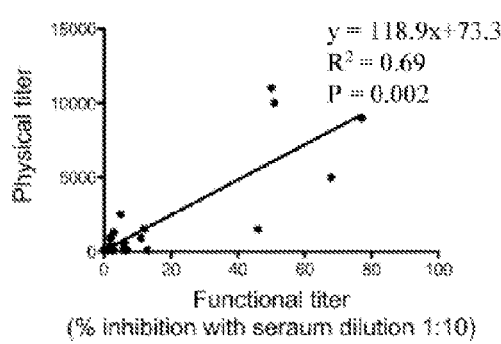
FIG. 11D

SEQUENCE LISTING

```
<160> NUMBER OF SEQ ID NOS: 9

<210> SEQ ID NO 1
<211> LENGTH: 480
<212> TYPE: PRT
<213> ORGANISM: Staphylococcus aureus

<400> SEQUENCE: 1

Ala Tyr Thr Val Thr Lys Pro Gln Thr Thr Gln Thr Val Ser Lys Ile
1               5                   10                  15

Ala Gln Val Lys Pro Asn Asn Thr Gly Ile Arg Ala Ser Val Tyr Glu
```

```
                20                  25                  30
Lys Thr Ala Lys Asn Gly Ala Lys Tyr Ala Asp Arg Thr Phe Tyr Val
             35                  40                  45
Thr Lys Glu Arg Ala His Gly Asn Glu Thr Tyr Val Leu Leu Asn Asn
 50                  55                  60
Thr Ser His Asn Ile Pro Leu Gly Trp Phe Asn Val Lys Asp Leu Asn
 65                  70                  75                  80
Val Gln Asn Leu Gly Lys Glu Val Lys Thr Thr Gln Lys Tyr Thr Val
                 85                  90                  95
Asn Lys Ser Asn Asn Gly Leu Ser Met Val Pro Trp Gly Thr Lys Asn
            100                 105                 110
Gln Val Ile Leu Thr Gly Asn Asn Ile Ala Gln Gly Thr Phe Asn Ala
            115                 120                 125
Thr Lys Gln Val Ser Val Gly Lys Asp Val Tyr Leu Tyr Gly Thr Ile
        130                 135                 140
Asn Asn Arg Thr Gly Trp Val Asn Ala Lys Asp Leu Thr Ala Pro Thr
145                 150                 155                 160
Ala Val Lys Pro Thr Thr Ser Ala Ala Lys Asp Tyr Asn Tyr Thr Tyr
                165                 170                 175
Val Ile Lys Asn Gly Asn Gly Tyr Tyr Tyr Val Thr Pro Asn Ser Asp
            180                 185                 190
Thr Ala Lys Tyr Ser Leu Lys Ala Phe Asn Glu Gln Pro Phe Ala Val
        195                 200                 205
Val Lys Glu Gln Val Ile Asn Gly Gln Thr Trp Tyr Tyr Gly Lys Leu
210                 215                 220
Ser Asn Gly Lys Leu Ala Trp Ile Lys Ser Thr Asp Leu Ala Lys Glu
225                 230                 235                 240
Leu Ile Lys Tyr Asn Gln Thr Gly Met Thr Leu Asn Gln Val Ala Gln
                245                 250                 255
Ile Gln Ala Gly Leu Gln Tyr Lys Pro Gln Val Gln Arg Val Pro Gly
            260                 265                 270
Lys Trp Thr Asp Ala Asn Phe Asn Asp Val Lys His Ala Met Asp Thr
        275                 280                 285
Lys Arg Leu Ala Gln Asp Pro Ala Leu Lys Tyr Gln Phe Leu Arg Leu
    290                 295                 300
Asp Gln Pro Gln Asn Ile Ser Ile Asp Lys Ile Asn Gln Phe Leu Lys
305                 310                 315                 320
Gly Lys Gly Val Leu Glu Asn Gln Gly Ala Ala Phe Asn Lys Ala Ala
                325                 330                 335
Gln Met Tyr Gly Ile Asn Glu Val Tyr Leu Ile Ser His Ala Leu Leu
            340                 345                 350
Glu Thr Gly Asn Gly Thr Ser Gln Leu Ala Lys Gly Ala Asp Val Val
        355                 360                 365
Asn Asn Lys Val Val Thr Asn Ser Asn Thr Lys Tyr His Asn Val Phe
    370                 375                 380
Gly Ile Ala Ala Tyr Asp Asn Asp Pro Leu Arg Glu Gly Ile Lys Tyr
385                 390                 395                 400
Ala Lys Gln Ala Gly Trp Asp Thr Val Ser Lys Ala Ile Val Gly Gly
                405                 410                 415
Ala Lys Phe Ile Gly Asn Ser Tyr Val Lys Ala Gly Gln Asn Thr Leu
            420                 425                 430
```

```
Tyr Lys Met Arg Trp Asn Pro Ala His Pro Gly Thr His Gln Tyr Ala
        435                 440                 445

Thr Asp Val Asp Trp Ala Asn Ile Asn Ala Lys Ile Ile Lys Gly Tyr
    450                 455                 460

Tyr Asp Lys Ile Gly Glu Val Gly Lys Tyr Phe Asp Ile Pro Gln Tyr
465                 470                 475                 480

<210> SEQ ID NO 2
<211> LENGTH: 120
<212> TYPE: PRT
<213> ORGANISM: Mus musculus

<400> SEQUENCE: 2

Gln Val Gln Leu Gln Gln Pro Gly Ala Glu Leu Val Gly Pro Gly Thr
1               5                   10                  15

Ser Val Lys Leu Ser Cys Lys Ser Ser Gly Tyr Thr Phe Thr Lys Tyr
            20                  25                  30

Trp Met His Trp Leu Lys Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Leu Gln Leu Ser Ser Leu Thr Ser Glu Asp Ser Ala Val Tyr Tyr Cys
                85                  90                  95

Ala Asn Tyr Tyr Gly Ser Tyr Tyr Asp Val Met Asp Phe Trp Gly Gln
            100                 105                 110

Gly Thr Ser Val Thr Val Ser Ser
        115                 120

<210> SEQ ID NO 3
<211> LENGTH: 108
<212> TYPE: PRT
<213> ORGANISM: Mus musculus

<400> SEQUENCE: 3

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Cys Phe Gly Ser Thr Leu Gln Ser Gly Thr Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln His Asn Glu Tyr Pro Leu
                85                  90                  95

Thr Phe Gly Ala Gly Thr Lys Leu Glu Leu Lys Arg
            100                 105

<210> SEQ ID NO 4
<211> LENGTH: 360
<212> TYPE: DNA
<213> ORGANISM: Mus musculus
```

```
<400> SEQUENCE: 4
caggtccaac tgcagcagcc tggggctgag ctggtggggc ctgggacttc agtgaagttg     60
tcctgcaagt cttctggcta caccttcacc aagtactgga tgcactggct aaagcagagg    120
cctggacaag gccttgagtg gatcggagtg attgatcctt ctgatagtta tactaactac    180
aatcaaaagt tcaagggcaa ggccacattg actgtagaca catcctccag cacagcctac    240
ctgcagctca gcagcctgac atctgaggac tctgcggtct attactgtgc caattactac    300
ggtagttact acgacgttat ggacttctgg ggtcaaggaa cctcagtcac cgtctcctca    360

<210> SEQ ID NO 5
<211> LENGTH: 324
<212> TYPE: DNA
<213> ORGANISM: Mus musculus

<400> SEQUENCE: 5
gatgtccaga taacccagtc tccatcttat cttgctgcat ctcctggaga gaccattact     60
attaattgca gggcaagtaa gagcattagc aaatatttag cctggtatca agagaaacct    120
gggaaaacga ataagcttct tatctgcttt ggatccactt tgcaatctgg aactccatca    180
aggttcagtg gcagtggatc tggtacagat ttcactctca ccatcagtag cctggagcct    240
gaagattttg caacgtatta ctgtcaacag cataatgaat acccgctcac gttcggtgct    300
gggaccaagc tggagctgaa acgt                                           324

<210> SEQ ID NO 6
<211> LENGTH: 21
<212> TYPE: DNA
<213> ORGANISM: Staphylococcus aureus

<400> SEQUENCE: 6
gcgattgatg gtgatacggt t                                               21

<210> SEQ ID NO 7
<211> LENGTH: 21
<212> TYPE: DNA
<213> ORGANISM: Staphylococcus aureus

<400> SEQUENCE: 7
agccaagcct tgacgaacta a                                               21

<210> SEQ ID NO 8
<211> LENGTH: 20
<212> TYPE: DNA
<213> ORGANISM: Mus musculus

<400> SEQUENCE: 8
agatgtgaat cagcaagcag                                                 20

<210> SEQ ID NO 9
<211> LENGTH: 20
<212> TYPE: DNA
<213> ORGANISM: Mus musculus

<400> SEQUENCE: 9
gcgcaagtta ggttttgtca                                                 20
```

ANTI-GLUCOSAMINIDASE PASSIVE IMMUNIZATION FOR *STAPHYLOCOCCUS AUREUS* INFECTIONS

This application is a national stage application under 35 U.S.C. 371 of International Patent Application No. PCT/US2012/062589, filed Oct. 30, 2012, which claims the benefit of U.S. Provisional Patent Application Ser. No. 61/554,777, filed Nov. 2, 2011, which is hereby incorporated by reference in its entirety.

This invention was made with government support under grant number R43AI085844 awarded by the National Institutes of Health. The government has certain rights in this invention.

FIELD OF THE INVENTION

The present invention relates to passive immunization against *Staphylococcus aureus* infection, particularly for the prevention or treatment of osteomyelitis and for implantation of an orthopedic implant or graft. Antibodies that bind specifically to *S. aureus* glucosaminidase and pharmaceutical compositions containing the same can be used for these purposes.

BACKGROUND OF THE INVENTION

There is a great need for novel interventions of chronic osteomyelitis (OM) as approximately 112,000 orthopedic device-related infections occur per year in the US, at an approximate hospital cost of $15,000-70,000 per incident (Darouiche, "Treatment of Infections Associated With Surgical Implants," *N. Engl. J. Med.* 350(14):1422-9 (2004)). Although improvements in surgical technique and aggressive antibiotic prophylaxis have decreased the infection rate following orthopedic implant surgery to 1-5%, osteomyelitis (OM) remains a serious problem and appears to be on the rise from minimally invasive surgery (Mahomed et al., "Rates and Outcomes of Primary and Revision Total Hip Replacement in the United States Medicare Population," *J. Bone Joint Surg. Am.* 85(A-1):27-32 (2003); WHO Global Strategy for Containment of Antimicrobial Resistance, 2001). The significance of this resurgence, 80% of which is due to *Staphylococcus aureus*, is amplified by the fact that ~50% of clinical isolates are methicillin resistant *S. aureus* (MRSA). While the infection rates for joint prosthesis and fracture-fixation devices have been only 0.3-11% and 5-15% of cases, respectively, over the last decade (Lew and Waldvogel, "Osteomyelitis," *Lancet* 364(9431):369-79 (2004); Toms et al., "The Management of Peri-Prosthetic Infection in Total Joint Arthroplasty," *J. Bone Joint Surg. Br.* 88(2):149-55 (2006)), this result may lead to amputation or death. Additionally, the popularization of "minimally invasive surgery" for elective total joint replacements (TJR) in which the very small incision often leads to complications from the prosthesis contacting skin during implantation, has markedly increased the incidence of OM (Mahomed et al., "Rates and Outcomes of Primary and Revision Total Hip Replacement in the United States Medicare Population," *J. Bone Joint Surg. Am.* 85(A-1):27-32 (2003); WHO Global Strategy for Containment of Antimicrobial Resistance, 2001). These infections require a very expensive two-stage revision surgery, and recent reports suggest that success rates could be as low as 50% (Azzam et al., "Outcome of a Second Two-stage Reimplantation for Periprosthetic Knee Infection," *Clin. Orthop. Relat. Res.* 467(7):1706-14 (2009)). However, the greatest concern is the emergence of drug resistant strains, most notably MRSA, which has surpassed HIV as the most deadly pathogen in North America, and continues to make the management of chronic OM more difficult, placing a great demand for novel therapeutic interventions. There is a great need for alternative interventional strategies, particularly for immune compromised elderly who are the primary recipients of TJR.

Presently, there are no prophylactic treatments that can protect high-risk patients from MRSA, most notably the aging "baby boomers" who account for most of the 1.5 million TJR performed annually in the United States. A vaccine that would decrease the MRSA incidence by 50-80% would not only reduce the number one complication of joint replacement and open fracture repair procedures, but also cut the healthcare burden by a similar amount.

Studies have documented that 80% of chronic OM is caused by *S. aureus*. These bacteria contain several factors that make them bone pathogens including several cell-surface adhesion molecules that facilitate their binding to bone matrix (Flock et al., "Cloning and Expression of the Gene for a Fibronectin-Binding Protein From *Staphylococcus aureus*," *Embo. J.* 6(8):2351-7 (1987)), toxins capable of stimulating bone resorption (Nair et al., "Surface-Associated Proteins From *Staphylococcus aureus* Demonstrate Potent Bone Resorbing Activity," *J. Bone Miner. Res.* 10(5):726-34 (1995)), through increased osteoclast activity (Marriott et al., "Osteoblasts Express the Inflammatory Cytokine Interleukin-6 in a Murine Model of *Staphylococcus aureus* Osteomyelitis and Infected Human Bone Tissue," *Am. J. Pathol.* 164(4):1399-406 (2004)). The rate-limiting step in the evolution and persistence of infection is the formation of biofilm around implanted devices (Costerton et al., "Bacterial Biofilms: A Common Cause of Persistent Infections," *Science* 284(5418):1318-22 (1999)). Shortly after implantation, a conditioning layer composed of host-derived adhesins (including fibrinogen, fibronectin, and collagen) forms on the surface of the implant and invites the adherence of free-floating bacteria derived from hematogenous seeding, including spread of infection from a contiguous area (the skin adjacent to a wound), surgical inoculation of bacteria into bone, or trauma coincident with significant disruption of the associated soft tissue bone envelope (Darouiche, "Treatment of Infections Associated With Surgical Implants," *N. Engl. J. Med.* 350(14):1422-9 (2004)). Over the next few days bacterial cell division, recruitment of additional planktonic organisms, and secretion of bacterial products (such as the glycocalyx) produces the biofilm. This biofilm serves as a dominant barrier to protect the bacteria from the action of antibiotics, phagocytic cells, antibodies and impairs lymphocyte functions (Gray et al., "Effect of Extracellular Slime Substance From *Staphylococcus epidermidis* on the Human Cellular Immune Response," *Lancet* 1(8373):365-7 (1984); Johnson et al., "Interference With Granulocyte Function By *Staphylococcus epidermidis* Slime," *Infect. Immun.* 54(1):13-20 (1986); Naylor et al., "Antibiotic Resistance of Biomaterial-Adherent Coagulase-Negative and Coagulase-Positive Staphylococci," *Clin. Orthop. Relat. Res.* 261:126-33 (1990)).

Another recent discovery is that *S. aureus* not only colonizes bone matrix, but is also internalized by osteoblasts in vitro (Ellington et al., "Involvement of Mitogen-Activated Protein Kinase Pathways in *Staphylococcus aureus* Invasion of Normal Osteoblasts," *Infect. Immun.* 69(9):5235-42 (2001)) and in vivo (Reilly et al., "In Vivo Internalization of *Staphylococcus aureus* by Embryonic Chick Osteoblasts," *Bone* 26(1):63-70 (2000)). This provides yet another layer of antibody and antibiotic resistance. This phase of infection occurs under conditions of markedly reduced metabolic activity and sometimes appears as so-called small-colony variants that likely accounts for its persistence (Proctor et al., "Persistent and Relapsing Infections Associated with Small-Colony Variants of *Staphylococcus aureus*," *Clin. Infect. Dis.* 20(1):95-102 (1995)). At this point the bacteria may also express phenotypic resistance to antimicrobial treatment, also explaining the high failure rate of short courses of therapy (Chuard et al., "Resistance of *Staphylococcus aureus* Recovered From Infected Foreign Body in Vivo to Killing by Antimicrobials," *J. Infect. Dis.* 163(6): 1369-73 (1991)). Due to these extensive pathogenic mechanism, OM is notorious for its tendency to recur even after years of quiescence, and it is accepted that a complete cure is an unlikely outcome (Mader and Calhoun, "Long-Bone Osteomyelitis Diagnosis and Management," *Hosp. Pract.* (*Off Ed*) 29(10):71-6,9,83 passim (1994)).

One of the key questions in the field of chronic OM is why current knowledge of factors that regulate chronic OM is so limited. Supposedly, the experimental tools necessary to elucidate bacterial virulence genes have been available for over a century. There are three explanations for this anomaly. First, although the total number of osteomyelitis cases is high, its incidence of 1-5% is too low for rigorous prospective clinical studies, with the possible exception of revision arthropasty. Second, it is well known that in vitro cultures rapidly select for growth of organisms that do not elaborate an extracellular capsule, such that biofilm biology can only be studied with in vivo models (Costerton et al., "Bacterial Biofilms: A Common Cause of Persistent Infections," *Science* 284(5418):1318-22 (1999)). This leads to the "greatest obstacle" in this field, which is the absence of a quantitative animal model that can assess the initial planktonic growth phase of the bacteria prior to biofilm formation. To date, much of the knowledge of its pathogenesis comes from animal models (Norden, "Lessons Learned From Animal Models of Osteomyelitis," *Rev. Infect. Dis.* 10(1):103-10 (1988)), which have been developed for the chicken (Daum et al., "A Model of *Staphylococcus aureus* Bacteremia, Septic Arthritis, and Osteomyelitis in Chickens," *J. Orthop. Res.* 8(6):804-13 (1990)), rat (Rissing et al., "Model of Experimental Chronic Osteomyelitis in Rats," *Infect. Immun.* 47(3):581-6 (1985)), guinea pig (Passl et al., "A Model of Experimental Post-Traumatic Osteomyelitis in Guinea Pigs," *J. Trauma* 24(4):323-6 (1984)), rabbit (Worlock et al., "An Experimental Model of Post-Traumatic Osteomyelitis in Rabbits," *Br. J. Exp. Pathol.* 69(2):235-44 (1988)), dog (Varshney et al., "Experimental Model of Staphylococcal Osteomyelitis in Dogs," *Indian J. Exp. Biol.* 27(9):816-9 (1989)), sheep (Kaarsemaker et al., "New Model for Chronic Osteomyelitis With *Staphylococcus aureus* in Sheep," *Clin. Orthop. Belot. Res.* 339:246-52 (1997)) and most recently mouse (Marriott et al., "Osteoblasts Express the Inflammatory Cytokine Interleukin-6 in a Murine Model of *Staphylococcus aureus* Osteomyelitis and Infected Human Bone Tissue," *Am. J. Pathol.* 164(4):1399-406 (2004)). While these models have been used to confirm the importance of bacterial adhesions identified from in vitro assays (Chuard et al., "Susceptibility of *Staphylococcus aureus* Growing on Fibronectin-Coated Surfaces to Bactericidal Antibiotics," *Antimicrob. Agents Chemother.* 37(4): 625-32 (1993); Buxton et al., "Binding of a *Staphylococcus aureus* Bone Pathogen to Type I Collagen," *Microb. Pathog.* 8(6):441-8 (1990); Switalski et al., "A Collagen Receptor on *Staphylococcus aureus* Strains Isolated From Patients With Septic Arthritis Mediates Adhesion to Cartilage," *Mol. Microbiol.* 7(1):99-107 (1993)), they do not have an outcome measure of in vivo growth, bacterial load, or osteolysis. Thus, they cannot be efficiently used to assess drug effects, bacterial mutants, and the role of host factors with transgenic mice.

Based on over 150 years of research, a clear paradigm to explain microbial pathogenesis has emerged. This model also applies to OM. The initial step of infection occurs when a unicellular bacterium invades the body. At this point the microbe must respond to environmental changes and express virulence genes that will help it defeat innate immunity and provide it with adhesin receptors to attach to the host. The bacterium is also dependent on the stochastic availability of host adhesins from necrotic tissue or a foreign body such as an implant. Successful completion of these steps leads to an exponential growth phase, which ceases at the point of nutrient exhaustion and/or the development of adaptive immunity. Following the exponential growth phase the bacteria are forced to persist under dormant growth conditions within the biofilm. However, at this point the infection is now chronic and cannot be eradicated by drugs or host immunity. Thus, the focus in this field has been on cell surface adhesins that specifically interact with extracellular matrix components known as MSCRAMMs (microbial surface components recognizing adhesive matrix molecules) (Patti et al., "MSCRAMM-Mediated Adherence of Microorganisms to Host Tissues," *Annu. Rev. Microbiol.* 48:585-617 (1994)). In fact, essentially all anti-*S. aureus* vaccines that have been developed to date have been directed against MSCRAMMs that are important for host tissue colonization and invasion. The goal of these vaccines is to generate antibodies that bind to these surface antigens, thereby inhibiting their attachment to host tissue. By opsinizing the bacterial surface, these antibodies can also mediate *S. aureus* clearance by phagocytic cells. Unfortunately, *S. aureus* has many adhesins, such that inhibition of one or more may not be sufficient to prevent bacterial attachment. Furthermore, bacterial clearance by phagocytic cells may be limited in avascular tissue, such that mAb may need additional antimicrobial mechanism of action to significantly reduce the in vivo planktonic growth of *S. aureus* and prevent the establishment of chronic OM or reinfection during revision total joint replacement surgery.

The present invention is directed to overcoming these and other deficiencies in the art.

SUMMARY OF THE INVENTION

A first aspect of the present invention is directed to a monoclonal antibody or binding portion thereof that binds specifically to a *Staphylococcus aureus* glucosaminidase and inhibits in vivo growth of *S. aureus*. In one embodiment, the monoclonal antibody or binding portion thereof includes one or both of a $V_H$ domain having the amino acid sequence of SEQ ID NO: 2 and a $V_L$ domain having the amino acid sequence of SEQ ID NO: 3.

A second aspect of present invention relates to a cell line that expresses a monoclonal antibody or binding portion of the present invention. In one embodiment, the cell line is a hybridoma cell line. In another embodiment, the cell line is a recombinant cell line that expresses the antibody.

A third aspect of the present invention relates to a pharmaceutical composition that includes a carrier and one or more monoclonal antibodies or binding portions of the present invention.

A fourth aspect of the present invention relates to a method of treating *S. aureus* infection that includes administering to a patient having a *S. aureus* infection an effective amount of a monoclonal antibody, binding portion, or pharmaceutical composition of the present invention.

A fifth aspect of the present invention relates to a method of treating osteomyelitis that includes administering to a patient having a S. aureus bone or joint infection an effective amount of a monoclonal antibody, binding portion, or pharmaceutical composition of the present invention.

A sixth aspect of the present invention relates to a method of introducing an orthopedic implant into a patient that includes administering to a patient in need of an orthopedic implant an effective amount of a monoclonal antibody, binding portion, or pharmaceutical composition of the present invention, and introducing the orthopedic implant into the patient. In this aspect of the present invention, the monoclonal antibody, binding portion, or pharmaceutical composition acts as a prophylactic agent. In certain embodiments, this aspect of the invention is directed to preventing OM or S. aureus reinfection during or subsequent to revision total joint replacement surgery.

A seventh aspect of the present invention relates to a method of assessing immunity of an individual against Staphylococcus aureus. The method includes exposing a Staphylococcus aureus glucosaminidase to a substrate of the glucosaminidase in the presence of sera from the individual; and assessing the activity of the glucosaminidase on the substrate after said exposing, wherein a relative decrease in glucosaminidase activity, relative to a negative control, indicates the degree of immunity conferred by the sera of the individual against Staphylococcus aureus.

Because S. aureus, and especially antibiotic resistant variants such as methicillin resistant S. aureus (MRSA), are the most common and challenging causes of Staphylococcus infections, the methods of the present invention aim to disrupt critical steps in the growth cycle of these microorganisms. The present invention also relates to a passive immunization for preventing infections in patients, for example, patients undergoing total joint replacement. The selected target for immunization is the glucosaminidase (Gmd) that S. aureus secretes to facilitate cytokinesis, the separation of cells during mitosis (Oshida et al., "A Staphylococcus aureus Autolysin that has an N-acetylmuramoyl-L-Alanine Amidase Domain and an Endo-beta-N-acetylglucosaminidase Domain: Cloning, Sequence Analysis, and Characterization," Proc Natl Acad Sci USA 92:285-9 (1995); Oshida et al., "Expression Analysis of the Autolysin Gene (atl) of Staphylococcus aureus," Microbiol Immunol 42:655-9 (1998); Sugai et al., "Localized Perforation of the Cell Wall by a Major Autolysin: atl Gene Products and the Onset of Penicillin-induced Lysis of Staphylococcus aureus," J Bacteriol 179:2958-62 (1997); and Yamada et al., "An Autolysin Ring Associated with Cell Separation of Staphylococcus aureus," J Bacteriol 178:1565-71 (1996), which are hereby incorporated by reference in their entirety).

To study and evaluate S. aureus infections, OM and various therapies directed towards Staphylococcus infections, a novel murine model of implant-associated OM in which a stainless steel pin is coated with S. aureus and implanted transcortically through the tibial metaphysic was used (Li et al., "Quantitative Mouse Model of Implant-Associated Osteomyelitis and the Kinetics of Microbial Growth, Osteolysis, and Humoral Immunity," J. Orthop. Res. 26(1):96-105 (2008), which is hereby incorporated by reference in its entirety). This model provides highly reproducible OM with Gram-positive biofilm, osteolysis, sequestrum/involucrum formation, and closely resembles clinical OM. Furthermore, in vivo bioluminescence imaging can be used to quantify the planktonic growth phase of the bacteria; real time quantitative-PCR(RTQ-PCR) can be used to determine nuc gene copy number in infected bone tissue to quantify the total bacteria load; and micro-CT can be used to quantify osteolysis.

Using the above-mentioned murine model of osteomyelitis, antibodies specific for Gmd have been identified as a conspicuous part of the successful immune response in the challenged mice. In addition, a vaccine comprising recombinant Gmd with N-terminal $His_6$ (Gmd-His) elicited at least partial immunity in the mouse model. The anti-Gmd antibodies can block S. aureus cell division by either directly blocking cell division or by recruiting host effectors such as phagocytes or complement at a vulnerable point in the cycle of cell division.

Experiments demonstrating the action of monoclonal antibody 4A12 and its derived human chimeric antibody are presented in the accompanying Examples. The Examples show that 4A12 and its mouse:human chimeric form suppress the growth of rapidly dividing S. aureus, as detected by light-scattering in growing cultures of S. aureus. Antibody 4A12 reduced the activity of Gmd to such a degree such that dividing cells failed to separate from each other. This effect was visually pronounced, dose-dependent, and consistent with a high affinity interaction between each antibody and Gmd. These effects demonstrate that the antibodies, raised against recombinant Gmd, react effectively with native Gmd and diminish its enzymatic activity. It is believed antibody 4A12 will inhibit in vivo S. aureus growth and infection in an in vivo mouse model, and the chimeric 4A12 will be similarly useful in human patients, particularly those undergoing an orthopedic implant such as a joint replacement or revision joint replacement.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

1B). Also shown are control mice that received a trans-tibial pin coated with *S. aureus* and treated with parenteral gentamicin (Gent), or received a sterile pin. The osteolytic area around the pin was quantified as previously described (Li et al., "Quantitative Mouse Model of Implant-Associated Osteomyelitis and the Kinetics of Microbial Growth, Osteolysis, and Humoral Immunity," *J. Orthop. Res.* 26(1): 96-105 (2008), which is hereby incorporated by reference in its entirety), and the data are presented as the mean+/−SD (* $p<0.05$ vs. Day 4; ** $p<0.05$ vs. Gent Day 18) (FIG. 1C). There was no difference in the osteolysis area between the gentamicin and sterile pin controls.

FIGS. 2A-H show the histology of trans-tibial implant-associated OM. H&E (Haematoxylin and Eosin stain) (FIGS. 2A-C), TRAP (Tartrate-Resistant Acid Phosphatase) (FIGS. 2D-F) and Gram stained (FIGS. 3G and 3H) sections of histology at the pin site (*) adjacent to the tibial cortex (#), 9 days after implantation of a sterile pin (FIGS. 2A, 2D, and 2G), or a pin coated with *S. aureus* (FIGS. 2B, 2C, 2E, 2F, and 2H). Of note is the new bone (h) that forms around the sterile pin (FIGS. 2A, 2D, and 2G) vs. the necrotic sequestrum (s) and involucrum (i) adjacent to the infected pin. While very few TRAP+ osteoclasts (yellow arrow heads) were present in the uninfected samples (FIG. 2D), numerous osteoclasts appear to be actively resorbing the cortex adjacent to the infected pin, and remodeling the new woven bone that is encasing the involucrum (FIGS. 2E and 2F). Gram staining confirmed the absence of bacteria in the specimens with the sterile pin (FIG. 2G) and their presence (black arrow heads) within the necrotic bone around the infected pins.

Figure 3A:
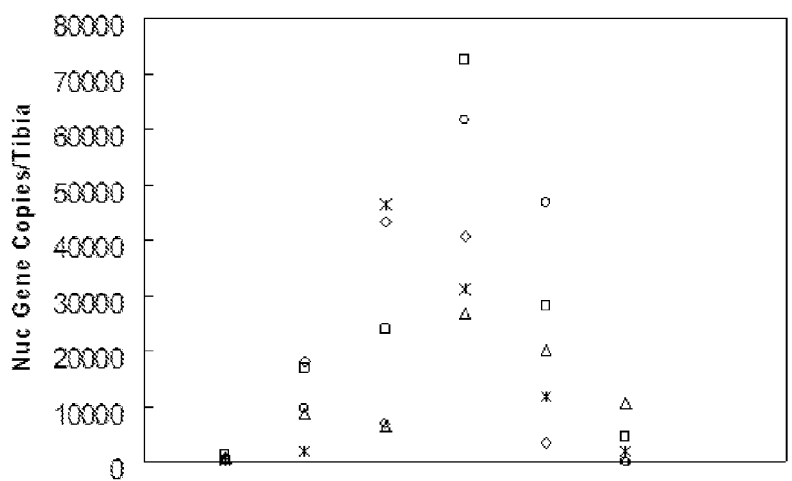
Figure 3B:
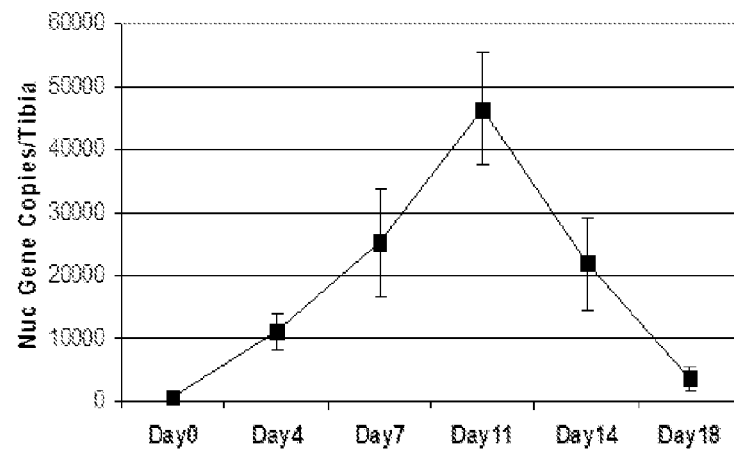
Figure 3C:
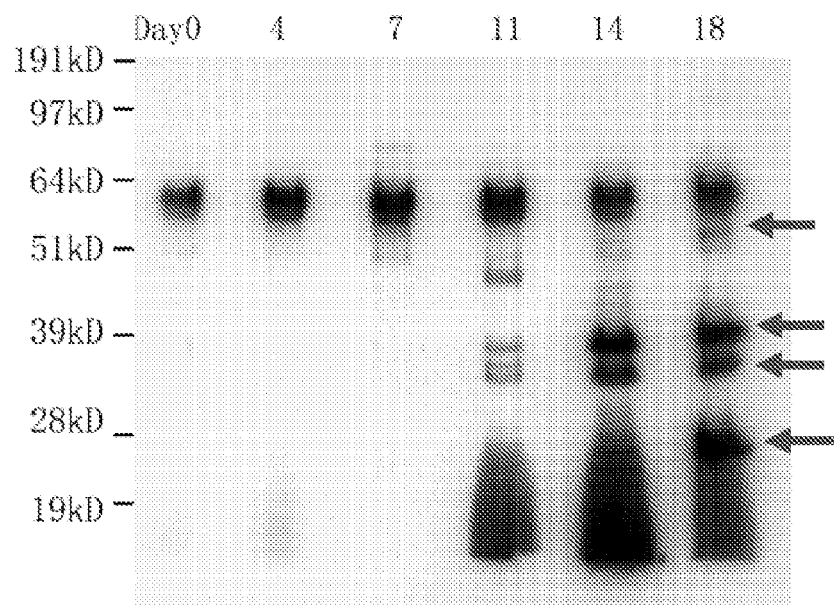

FIGS. 3A-C show the inverse correlation between bacterial load and humoral immunity against *S. aureus* antigens during the establishment of chronic osteomyelitis. A time course study was performed in which mice were given an infected transcortical pin containing $1\times10^6$ CFU of *S. aureus* in their tibia and sacrificed on the indicated day. At sacrifice, DNA was purified from the infected tibia and RTQ-PCR was performed to determine the Ct values for *S. aureus* nuc. Using a standard curve shown, this number was converted to the recoverable nuc genes per tibia. To control for the integrity of the samples, the recoverable nuc gene per tibia value was standardized to the Ct value for mouse β-actin for each sample. From this conversion the bacterial load was derived as "Nuc Gene Copies/Tibia." The data from each mouse is shown in FIG. 3A as an individual point, and the mean+/−SD for each time point (n=5) is presented in FIG. 3B. To assess the development of anti-*S. aureus* specific antibodies during the establishment of OM, serum was taken from each mouse in the group that was sacrificed on day 18, before infection (day 0) and on days 4, 7, 11, 14 and 18 after infection. This serum was used as the primary antibody in Western blots of total *S. aureus* extract that were then probed with HRP-conjugated antibodies that are specific for mouse IgG as shown in FIG. 3C. The data show that there is a steady increase in bacterial growth from day 0 to day 11, when the host first develops specific antibodies against the bacteria. As the titer of the anti-*S. aureus* antibodies increases the bacterial load drops, suggesting that the antibodies are protective. The Western blots also clearly identify four immuno-dominant antigens of 26, 34, 38 and 56 kDa (arrows). It has also been demonstrated that Xen 29 also induces antibodies against these same 26, 34, 38 and 56 kDa proteins.

Figures 4A, 4B, 4C:
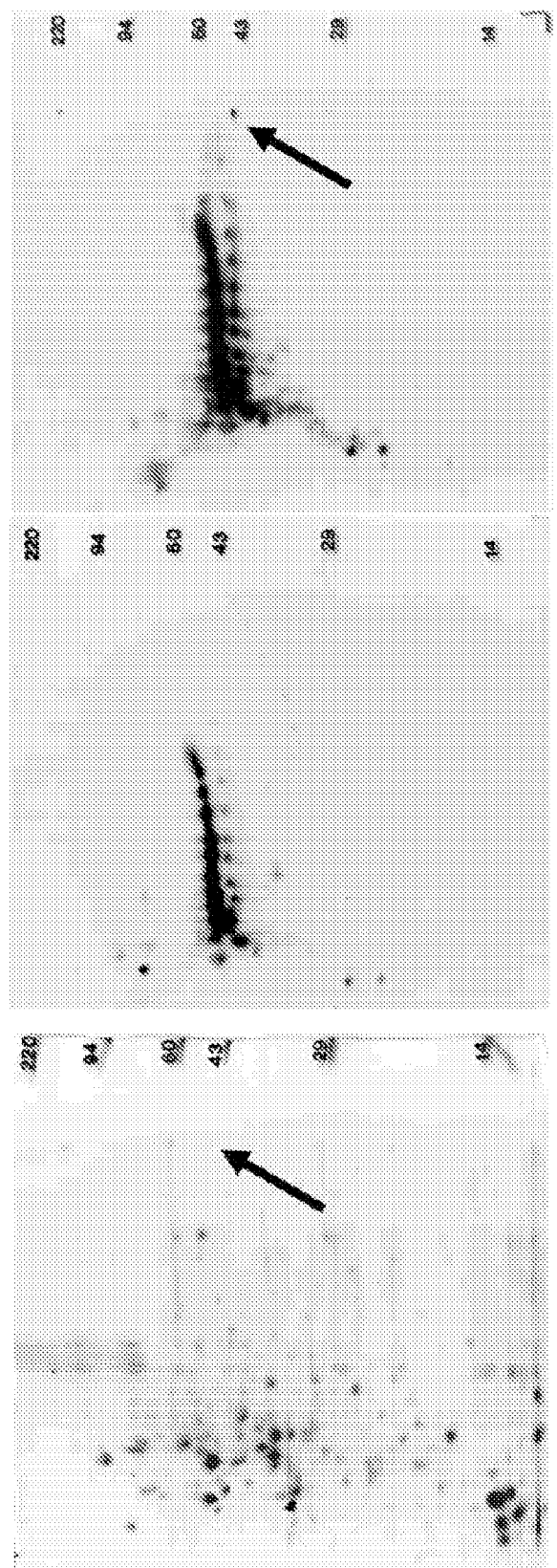

FIGS. 4A-C show that glucosaminidase of *S. aureus* autolysin is the 56 kDa immuno-dominant antigen. To elucidate the molecular identity of the novel *S. aureus* antigens identified in FIG. 3, subtractive immunoblot analysis of 2D-SDS-PAGE of whole cell extract was performed with pre-immune and day 14 immune sera. Three 2D gels were run after isoelectric focusing (pH 4.0-10.0). The first was Coomassie blue-stained (FIG. 4A). The others were Western blotted with either day 0 (FIG. 4B) or day 14 sera (FIG. 4C). In addition to the background reactivity, the immune serum detected a specific polypeptide (~53 kDa; pH 9: arrow). The 53 kDa spot was removed from the Coomassie gel, digested with trypsin, and analyzed by MALDI, which resolved 70 individual peptide peaks. The amino acid sequence from every peptide was a 100% match with the known sequence of the glucosaminidase of *S. aureus* autolysin, which is 53.6 kDa and has a pI of 9.66.

Figures 5A, 5B:
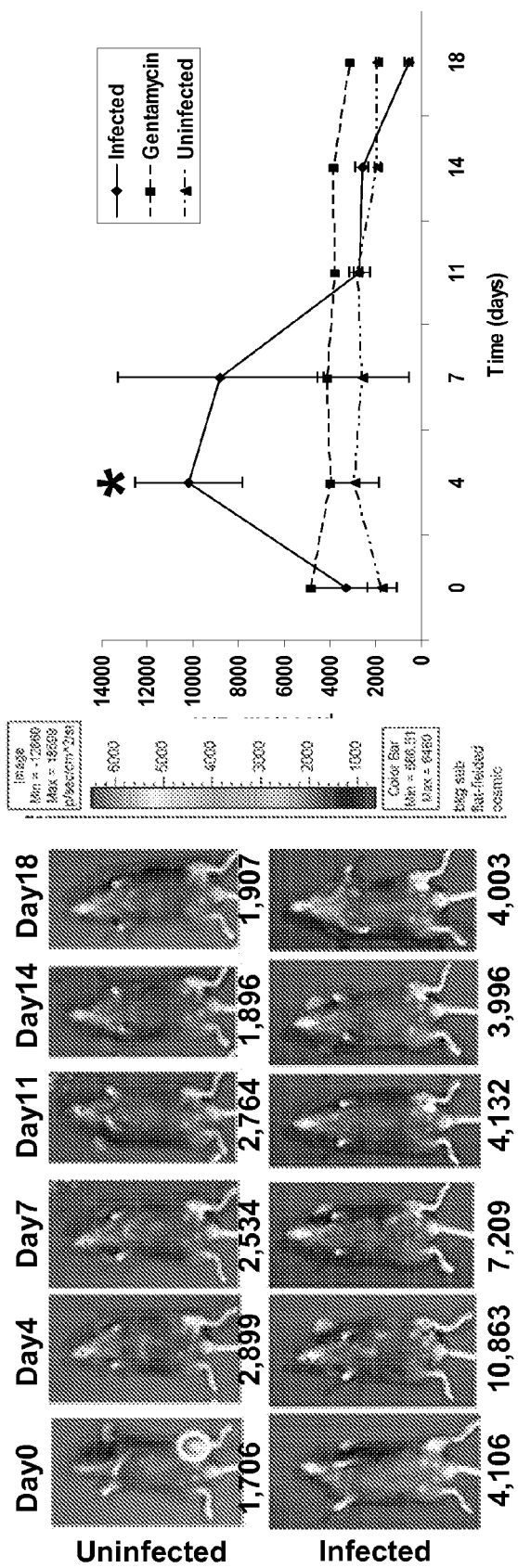

FIGS. 5A-B show bioluminescent imaging (BLI) quantification of bacterial growth during the establishment of chronic osteomyelitis. FIG. 5A shows BLI levels (p/sec/cm$^2$/sr) at the site of infection and was assessed longitudinally in mice that received a sterile trans-tibial pin (Uninfected), or a pin coated with Xen 29 *S. aureus* (Infected) and were imaged on the indicated day. The circle in the top left image highlights the 1.5 cm diameter region of interest (ROI) that was assessed for BLI in each mouse at each time point. FIG. 5B shows the data from mice (N=5) that were Uninfected, Infected or infected and treated with parenteral antibiotics (Gentamycin) and were assessed for BLI longitudinally at the indicated time following surgery. The data are presented as the mean+/−SD (* Significantly greater vs. Day 0; $p<0.05$).

Figure 6B:
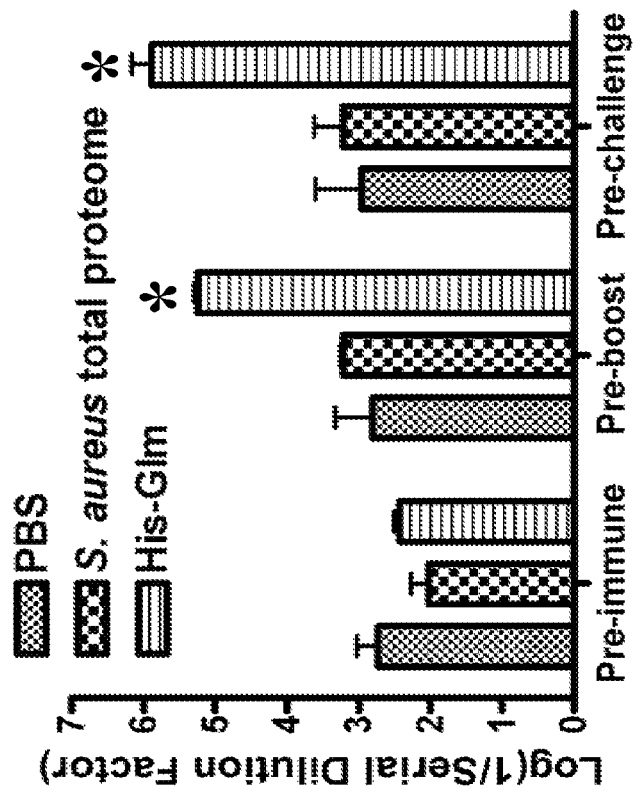
Figure 6A:
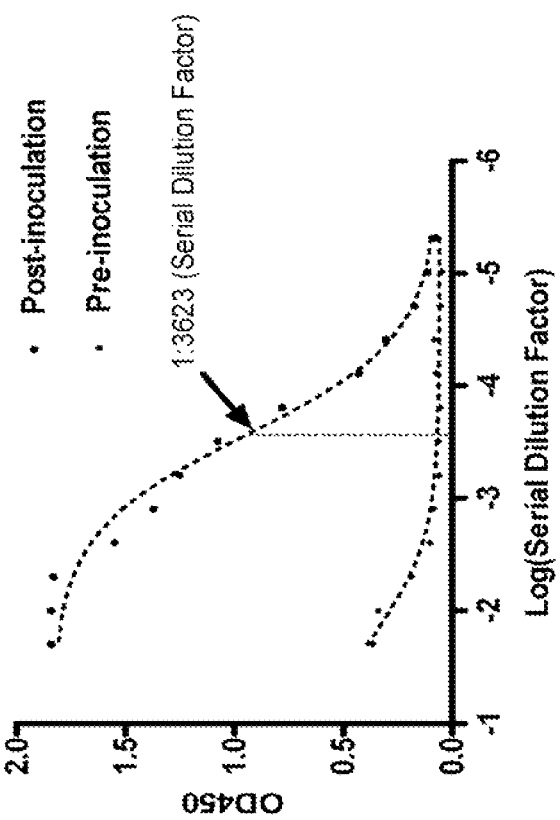

FIGS. 6A-B show that functional anti-Gmd ELISA demonstrated the efficacy of recombinant Gmd vaccine. FIG. 6A shows serum ELISA in which His-Gmd was used as the antigen to assay anti-Gmd antibody titers in mouse serum which was generated using a known high titer anti-sera from *S. aureus* infected mice. The serial dilution factor (X axis) and absorbance reading at 450 nm (Y axis) of the serial 2-fold diluted sera samples are plotted in the XY plane using GraphPad Prism 4 software. The functional titer (1:3623) is extrapolated from the inflection point (arrow) of the dilution curve. FIG. 6B shows the ELISA used to determine the titers of anti-Gmd antibodies in the sera of mice pre-immunization, pre-boost and pre-challenge with the indicated vaccine. Note that only mice immunized with the His-Gmd vaccine obtained high titers.

FIGS. 7A-C show that recombinant His-Gmd vaccine protects mice from implant-associated OM. The mice (n=20) were challenged with a Xen29 infected transtibial pin as described in the accompanying Examples, BLI was performed on day 3, and the mice were euthanized for nuc RTQ-PCR on day 11. An image of the BLI from a representative mouse in Group 1 & 3 is shown (FIG. 7A), and the mean+/−SD is presented to show the significant reduction BLI (FIG. 7B). This translated into a significant decrease in amplifiable nuc genes (mean+/−SD) on day 11 (FIG. 7C).

Figure 8:
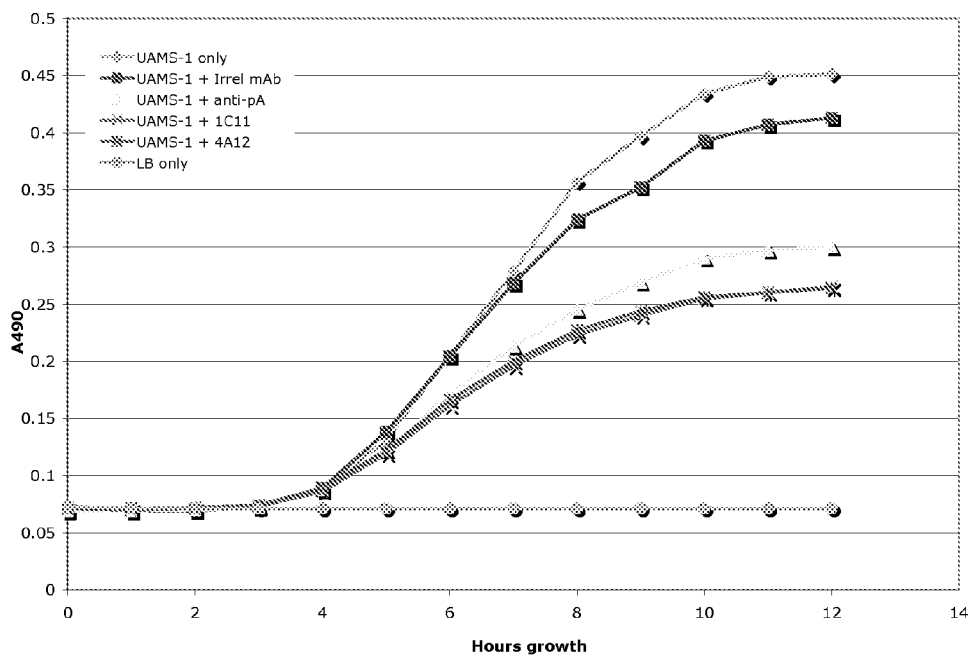

FIG. 8 is a graph comparing *S. aureus* in vitro growth inhibition using mAbs 1C11 and 4A12. 1C11 is described in PCT application Publication No. WO2011/140114, which is hereby incorporated by reference in its entirety. 100 cfu of *S. aureus* (UAMS-1) from a culture in log-phase growth were incubated at 37° C. with 50 mg/mL in LB medium of either irrelevant IgG mAb (CTL), a mAb against *S. aureus* protein A (Anti-Spa), or 4A12 or 1C11 anti-Gmd mAbs. Growth was monitored by light scattering at 490 nm at the indicated intervals. mAbs 4A12 and 1C11 produced comparable and significant in vitro growth inhibition.

FIGS. 9A-D are images illustrating anti-Gmd mAb 4A12 inhibition of *S. aureus* binary fission. *S. aureus* (Xen29) was cultured in liquid Luria Broth (LB) media in the presence of an irrelevant IgG mAb (CTL), a mAb against *S. aureus* protein A (Anti-Spa), or 4A12 and 1C11 anti-Gmd mAbs. After 12 hr of culture at 37° C., aliquots of the suspension culture were harvested for scanning electron microscopy. Representative photographs are presented to illustrate the lack of effects of the CTL and Anti-Spa mAb on binary fission, as the daughter bacteria have clearly defined cell membranes (white arrows). In contrast, both 4A12 and 1C11 inhibit binary fission as evidenced by the extended division plate between the daughter bacteria (red arrows). Evidence of greater inhibition by 4A12 vs. 1C11 is provided by the absence of a clearly visible cleavage plate.

Figure 10:
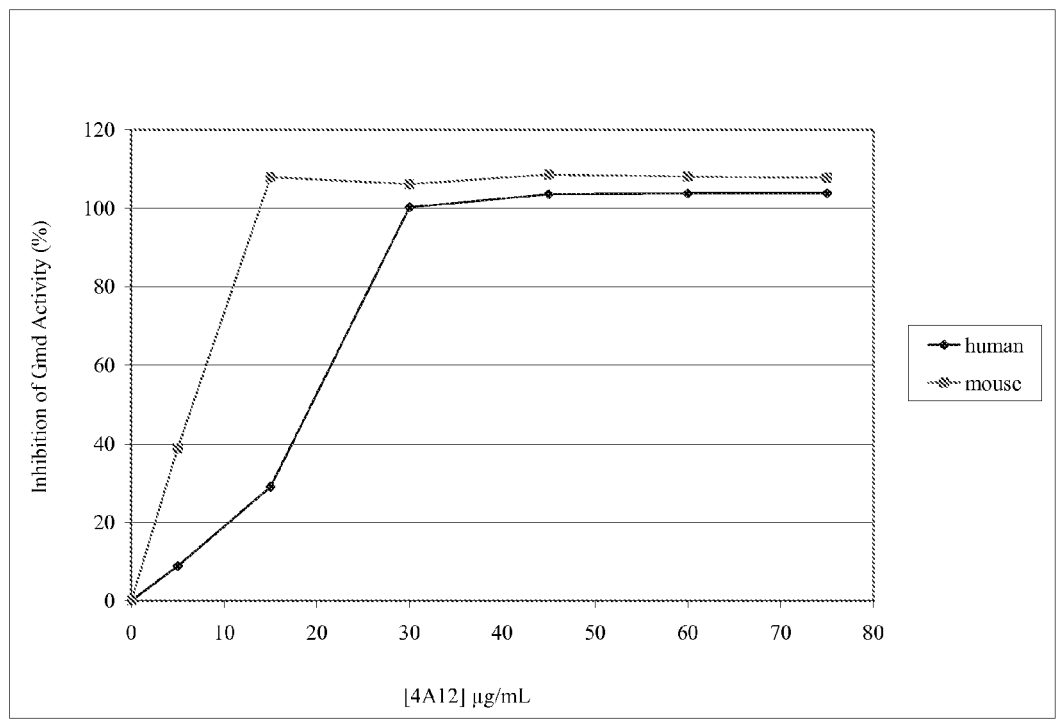
Figure 9A:
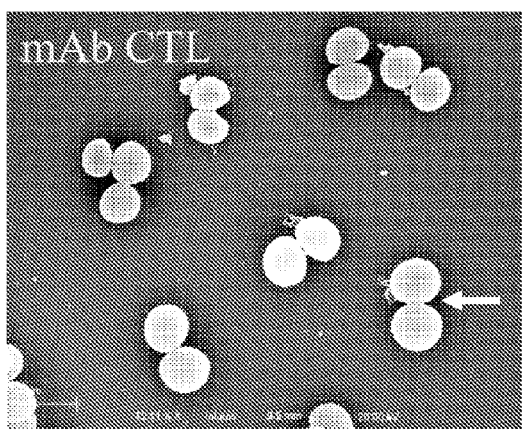
Figure 9B:
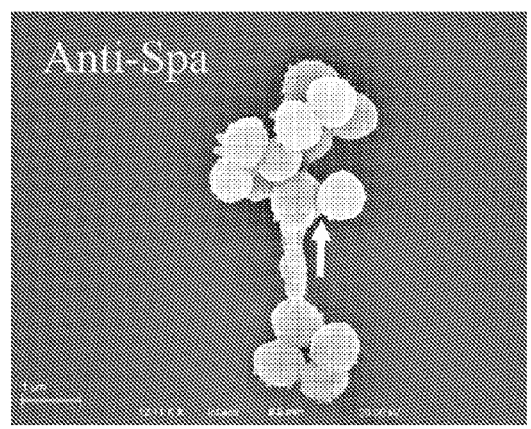
Figure 9C:
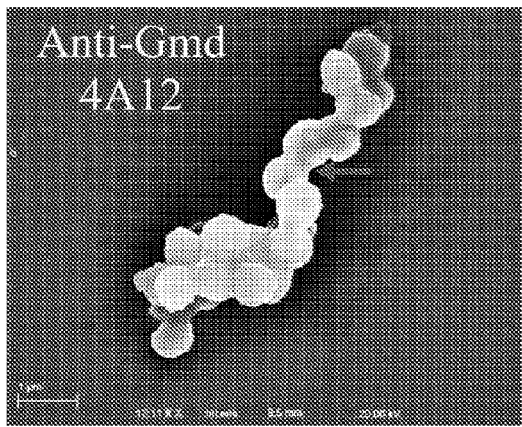
Figure 9D:
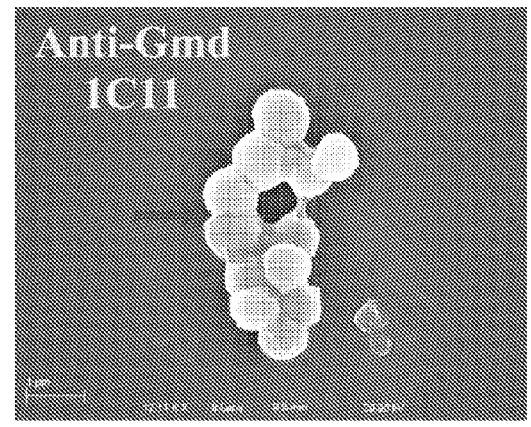

FIG. 10 is graph comparing the ability of mouse and human:mouse chimeric 4A12 monoclonal antibodies to inhibit enzymatic activity of Gmd. Mouse IgG1 4A12 and its chimeric form with the human IgG1 heavy chain and human kappa light chain were incubated at the indicated concentrations with Gmd in the presence of heat-killed *M. luteus*, a substrate for Gmd activity. After incubation at 37° C. for 60 minutes, the degree of cell lysis was measured by comparing the light scattering at 490 nm compared to that at t=0. Inhibition of Gmd was calculated using the formula: % Inhibition=$100(1-(\Delta 60$ mAb/$\Delta 60$no mAb)). $\alpha 60$ mAb=the change in $A_{490}$ measured in the presence of the mAb after 60 minutes; 460no mAb=the change in $A_{490}$ measured in the absence of the mAb after 60 minutes.

FIGS. 11A-C show assays of the functional titer of anti-Gmd antibodies. The functional titer was determined via an *M. luteus* cell wall digestion assay (FIG. 11A) where the box indicates the effective concentration of His-Gmd as 3.5 µg/ml. The sensitivity of the assay was determined as % inhibition of the 3.5 µg/ml His-Gmd with dilutions of purified 1C11 mAb in which the titer is the inflection point (FIG. 11B arrows). FIG. 11C demonstrates the specificity of the functional assays with sera dilutions 1:10 from naïve mice, challenged mice and immunized mice. FIG. 11D shows linear regression analysis between the physical and functional titers (% inhibition at a serum dilution of 1:10 in PBS; p-value<0.0002 Pearson's correlation coefficient).

Figure 12A:
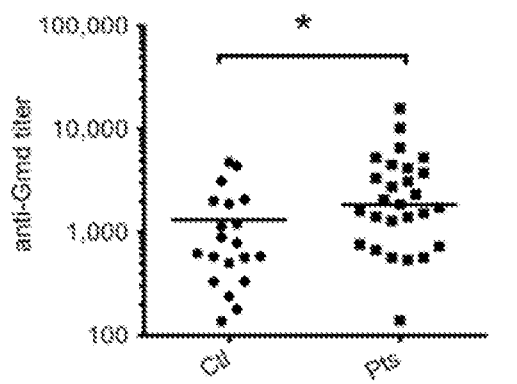
Figure 12B:
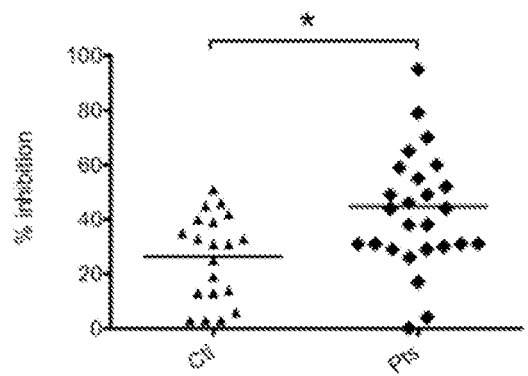
Figure 12C:
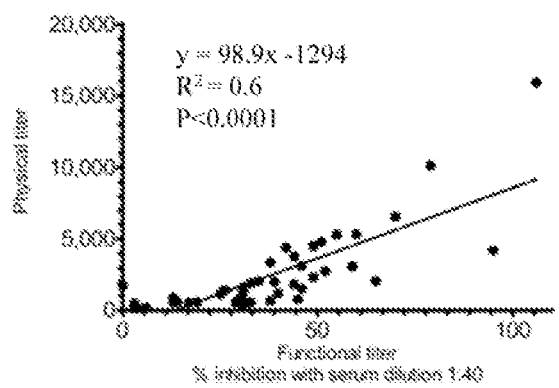

FIGS. 12A-B show the difference in physical (*p<0.02) and functional titers (**p<0.0001) between infection patients and healthy controls. FIG. 12C shows the linear regression analysis between the physical and functional titers (*p<0.0001).

Figure 13:
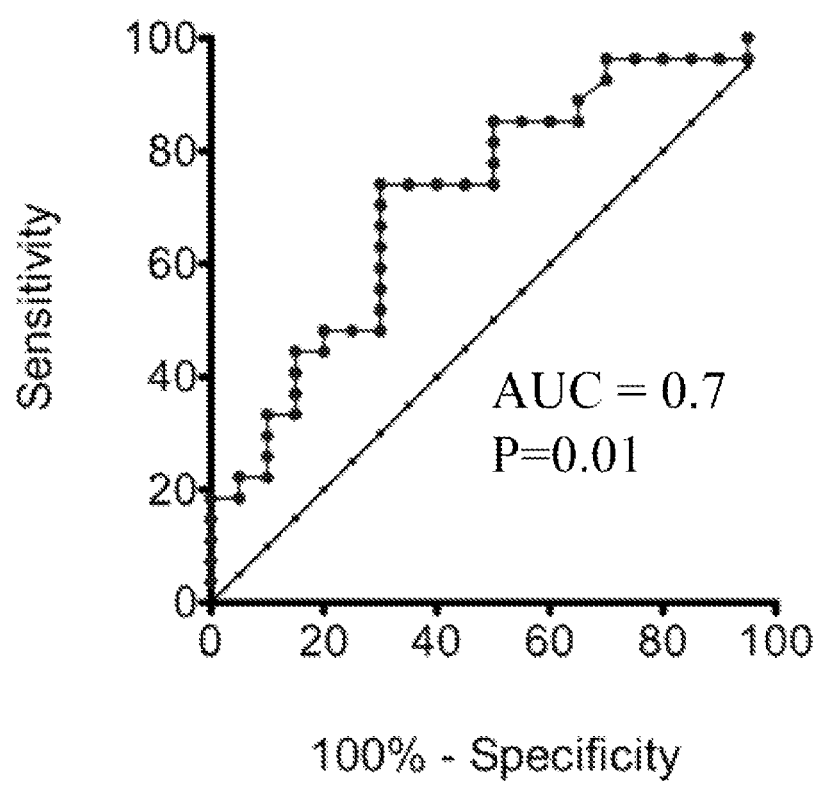

FIG. 13 shows the receiver-operator characteristics (ROC) curve of anti-Gmd antibodies.

DETAILED DESCRIPTION OF THE INVENTION

In one aspect, the present invention relates to a monoclonal antibody that binds specifically to a *Staphylococcus aureus* glucosaminidase and inhibits in vivo growth of *S. aureus*. The monoclonal antibody of the present invention can be such that it targets *S. aureus* that is methicillin resistant.

As used herein, the term "antibody" is meant to include immunoglobulins derived from natural sources or from recombinant sources, as well as immunoreactive portions (i.e. antigen binding portions) of immunoglobulins. The monoclonal antibodies of the present invention may exist in or can be isolated in a variety of forms including, for example, substantially pure monoclonal antibodies, antibody fragments or binding portions, chimeric antibodies, and humanized antibodies (Ed Harlow and David Lane, USING ANTIBODIES: A LABORATORY MANUAL (Cold Spring Harbor Laboratory Press, 1999), which is hereby incorporated by reference in its entirety).

The monoclonal antibodies of the present invention are characterized by specificity for binding to *S. aureus* glucosaminidase or fragments thereof. The antibody specifically binds to an immuno-dominant epitope in the glucosaminidase (Gmd) sub-unit of *S. aureus* autolysin (Atl). These monoclonal antibodies inhibit in vivo growth of *S. aureus*.

Immuno-dominant antigen is a part of the antigenic determinant that is most easily recognized by the immune system and thus exerts the most influence on the specificity of the induced antibody. An "immuno-dominant epitope" refers to the epitope on an antigen that selectively provokes an immune response in a host organism to the substantial exclusion of other epitopes on that antigen.

Usually, the antigen likely to carry an immuno-dominant epitope can be identified by selecting antigens on the outer surface of the pathogenic organism. For example, most simple organisms, such as fungi, bacteria and viruses have one or two proteins that are exposed on the outer surface of the pathogenic organism. These outer surface proteins are most likely to carry the appropriate antigen. The proteins most likely to carry an immuno-dominant epitope can be identified in a Western assay in which total protein is run on a gel against serum from an organism infected with the pathogenic organism. Bound antibodies from the serum are identified by labeled anti-antibodies, such as in one of the well-known ELISA techniques. The immuno-dominant epitope can be identified by examining serum from a host organism infected with the pathogenic organism. The serum is evaluated for its content of antibodies that bind to the identified antigens that are likely to cause an immune response in a host organism. If an immuno-dominant epitope is present in these antigens, substantially all antibodies in the serum will bind to the immuno-dominant epitope, with little binding to other epitopes present in the antigen.

Atl is one of the catalytically distinct peptidoglycan hydrolases in *S. aureus* that is required to digest the cell wall during mitosis (Baba and Schneewind, "Targeting of Muralytic Enzymes to the Cell Division Site of Gram-Positive Bacteria: Repeat Domains Direct Autolysin to the Equatorial Surface Ring of *Staphylococcus aureus*," *EMBO. J.* 17(16): 4639-46 (1998), which is hereby incorporated by reference in its entirety). In addition to being an essential gene for growth, scanning electron microscopy studies have demonstrated that anti-Atl antibodies bound to *S. aureus* during binary fission localize to regions of the bacteria that are not covered by the cell wall (Yamada et al., "An Autolysin Ring Associated With Cell Separation of *Staphylococcus aureus*," *J. Bacteria* 178(6):1565-71 (1996), which is hereby incorporated by reference in its entirety).

The Atl enzyme is comprised of an amidase (62 kD) and glucosaminidase (53 kd)), which are produced from the same Atl precursor protein via a cleavage process (Baba and Schneewind, "Targeting of Muralytic Enzymes to the Cell Division Site of Gram-Positive Bacteria: Repeat Domains Direct Autolysin to the Equatorial Surface Ring of *Staphylococcus aureus*," Embo. J. 17(16):4639-46 (1998); Komatsuzawa et al., "Subcellular Localization of the Major Autolysin, ATL and Its Processed Proteins in *Staphylococcus aureus*," *Microbiol Immunol.* 41:469-79 (1997); Oshida et al., "A *Staphylococcus aureus* Autolysin That Has an N-acetylmuramoyl-L-alanine Amidase Domain and an Endo-beta-N-acetylglucosaminidase Domain: Cloning, Sequence Analysis, and Characterization," *Proc. Nat'l.*

*Acad. Sci. U.S.A.* 92(1):285-9 (1995), which are hereby incorporated by reference in their entirety). The autolysin is held to the cell wall by three ~150 amino acid cell wall binding domains R1, R2, and R3. In the final maturation step, proteolytic cleavage separates the aminidase domain and its associated R1 and R2 domains from the glucosaminidase and its associated N-terminal R3 domain.

By way of example, and without limitation, one exemplary *Staphylococcus aureus* glucosaminidase contains the amino acid sequence of SEQ ID NO: 1 below.

```
AYTVTKPQTT QTVSKIAQVK PNNTGIRASV YEKTAKNGAK

YADRTFYVTK ERAHGNETYV LLNNTSHNIP LGWFNVKDLN

VQNLGKEVKT TQKYTVNKSN NGLSMVPWGT KNQVILTGNN

IAQGTFNATK QVSVGKDVYL YGTINNRTGW VNAKDLTAPT

AVKPTTSAAK DYNYTYVIKN GNGYYYVTPN SDTAKYSLKA

FNEQPFAVVK EQVINGQTWY YGKLSNGKLA WIKSTDLAKE

LIKYNQTGMT LNQVAQIQAG LQYKPQVQRV PGKWTDANFN

DVKHAMDTKR LAQDPALKYQ FLRLDQPQNI SIDKINQFLK

GKGVLENQGA AFNKAAQMYG INEVYLISHA LLETGNGTSQ

LAKGADVVNN KVVTNSNTKY HNVFGIAAYD NDPLREGIKY

AKQAGWDTVS KAIVGGAKFI GNSYVKAGQN TLYKMRWNPA

HPGTHQYATD VDWANINAKI IKGYYDKIGE VGKYFDIPQY
```

In SEQ ID NO: 1, underlined residues correspond to residues 783 to 931 of the encoded autolysin, and represent the R3 domain. The remaining C-terminal residues (not underlined) correspond to the catalytic glucosaminidase domain.

The *S. aureus* Gmd can be synthesized by solid phase or solution phase peptide synthesis, recombinant expression, or can be obtained from natural sources. Automatic peptide synthesizers are commercially available from numerous suppliers, such as Applied Biosystems, Foster City, Calif. Standard techniques of chemical peptide synthesis are well known in the art (see e.g., SYNTHETIC PEPTIDES: A USERS GUIDE 93-210 (Gregory A. Grant ed., 1992), which is hereby incorporated by reference in its entirety). Protein or peptide production via recombinant expression can be carried out using bacteria, such as *E. coli*, yeast, insect or mammalian cells and expression systems. Procedures for recombinant protein/peptide expression are well known in the art and are described by Sambrook et al, Molecular Cloning: A Laboratory Manual (C.S.H.P. Press, NY 2d ed., 1989).

Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

In certain embodiments the monoclonal antibody of the present invention binds to a conserved epitope of *Staphylococcus aureus* glucosaminidase with an affinity greater than $10^{-9}$ M. As used herein, "epitope" refers to the antigenic determinant of *Staphylococcus aureus* glucosaminidase that is recognized by the monoclonal antibody. The epitope recognized by the antibody of the present invention may be a linear epitope, i.e., the primary structure of the amino acid sequence of glucosaminidase. Alternatively, the epitope recognized by the antibody of the present invention may be a non-linear or conformational epitope, i.e., the tertiary structure of glucosaminidase.

In certain embodiments, the monoclonal antibodies may bind specifically to the catalytic domain of the Gmd. One exemplary antibody of the present invention is monoclonal antibody 4A12. Because 4A12 did not react with linear Gmd fragments in an epitope mapping assay, it is believed that 4A12 recognizes a conformational epitope that likely lies within the catalytic domain.

In other embodiments, the monoclonal antibodies may bind specifically to the R3 domain. Examples of monoclonal antibodies that bind to the R3 domain include, without limitation, mAbs 1C11, 1E12, 2D11, 3A8, and 3H6.

In certain embodiments, the monoclonal antibody of the present invention possesses *S. aureus* Gmd inhibitory activity, whereby the monoclonal antibody inhibits the activity of Gmd by at least 20%, at least 30%, at least 40% or at least 50%. In other embodiments, the monoclonal antibody inhibits the activity of Gmd by at least 60%, at least 70%, or at least 80%. Monoclonal antibody 4A12 possesses anti-Gmd inhibitory activity approaching nearly complete inhibition (>99%).

Inhibition of Gmd activity can be measured in vitro. According to one approach, Gmd is first pre-titered to determine the concentration that will yield about a 50% reduction in $A_{490}$ in 60 minutes. Then 50 nl of antibody diluted in PBST is added to each well of a 96-well microtiter plate followed by 50 nl, of appropriately diluted Gmd, and the mixture allowed to incubate for 5 or more minutes, and finally 100 µL of 0.15% mL is added and the initial $A_{490}$ measured. The plate is incubated at 37° C. and the $A_{490}$ measured at 30 and 60 minutes. Percent inhibition is calculated as $100 \cdot (1-(\Delta_{60}A_{490}$ inhibitor$/\Delta_{60}A_{490}$ no inhibitor control$))$.

In certain embodiments, the monoclonal antibody of the present invention possesses an ability to cause clustering or clumping of *S. aureus*, cell-independent lysis of *S. aureus*, or both. Examples of antibodies that possess an ability to cause clumping of *S. aureus* include, without limitation, monoclonal antibodies 4A12, 1C11, 1E12, 2D11, 3A8, and 3H6. One example of a lytic antibody is monoclonal antibody 1C11.

Monoclonal antibody 4A12, or binding fragments thereof, can be used alone or in combination with one or more of monoclonal antibodies 1C11, 1E12, 2D11, 3A8, and 3H6 (see PCT application Publication No. WO2011/140114, which is hereby incorporated by reference in its entirety).

The monoclonal antibodies of the present invention also inhibit in vivo growth of *S. aureus*. Inhibition of in vivo growth of *S. aureus* can be measured according to a number of suitable standards. In one such embodiment, the in vivo growth of *S. aureus* can be assessed according to a bioluminescence assay of the type described in the accompanying Examples. Specifically, bioluminescent *S. aureus* (Xen 29; ATCC 12600) (Francis et al., "Monitoring Bioluminescent *Staphylococcus aureus* Infections in Living Mice Using a Novel luxABCDE Construct," Infect. Immun. 68(6):3594-600 (2000); see also Contag et al., "Photonic Detection of Bacterial Pathogens in Living Hosts," Mol. Microbiol. 18(4):593-603 (1995), each of which is hereby incorporated by reference in its entirety) is used to dose a transtibial implant with 500,000 CFU prior to surgical implant. Five week old female BALB/cJ mice can receive an intraperitoneal injection of saline (n=10) or 1 mg of purified antibody in 0.25 ml saline 3 days prior to surgery. The mice can be imaged to assess bioluminescence on various days (e.g., 0, 3, 5, 7, 11, and 14) and a comparison of BLI images can be compared to assess whether the antibody inhibits in vivo growth of S. aureus relative to the saline control.

According to one embodiment, the monoclonal antibody comprises a $V_H$ domain comprising the amino acid sequence of SEQ ID NO: 2 as follows:

QVQLQQPGAELVGPGTSVKLSCKSSGYTETKYWMHWLKQRPGQ

GLEWIGVIDPSDSYTNYNQKFKGKATLTVDTSSSTAYLQLSSL

TSEDSAVYYCANYYGSYYDVMDFWGQGTSVTVSS

According to one embodiment, the monoclonal antibody comprises a $V_L$ domain comprising the amino acid sequence of SEQ ID NO: 3 as follows:

DVQITQSPSYLAASPGETITINCRASKSISKYLAWYQEKPGKT

NKLLICFGSTLQSGTPSRFSGSGSGTDFTLTISSLEPEDFATY

YCQQHNEYPLTFGAGTKLELKR

Monoclonal antibody 4A12 possesses the $V_H$ domain of SEQ ID NO: 2 and the $V_L$ domain of SEQ ID NO: 3.

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the invention or the synthesis of an amino acid specifying the antibody, where the DNA or amino acid sequence has been obtained using synthetic DNA or amino acid sequence technology which is available and well known in the art.

The monoclonal antibody of the present invention can be humanized. Humanized antibodies are antibodies that contain minimal sequences from non-human (e.g. murine) antibodies within the variable regions. Such antibodies are used therapeutically to reduce antigenicity and human anti-mouse antibody responses when administered to a human subject. In practice, humanized antibodies are typically human antibodies with minimum to no non-human sequences. A human antibody is an antibody produced by a human or an antibody having an amino acid sequence corresponding to an antibody produced by a human.

An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," Nature 321:522-525 (1986); Riechmann et al., "Reshaping Human Antibodies for Therapy," Nature 332:323-327 (1988); Verhoeyen et al., "Reshaping Human Antibodies: Grafting an Antilysozyme Activity," Science 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Humanized antibodies can be produced using various techniques known in the art Immortalized human B lymphocytes immunized in vitro or isolated from an immunized individual that produce an antibody directed against a target antigen can be generated (see e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the humanized antibody can be selected from a phage library, where that phage library expresses human antibodies (Vaughan et al., "Human Antibodies with Sub-Nanomolar Affinities Isolated from a Large Non-immunized Phage Display Library," Nature Biotechnology, 14:309-314 (1996); Sheets et al., "Efficient Construction of a Large Nonimmune Phage Antibody Library: The Production of High-Affinity Human Single-Chain Antibodies to Protein Antigens," Proc. Nat'l. Acad. Sci. U.S.A. 95:6157-6162 (1998); Hoogenboom et al., "By-passing Immunisation. Human Antibodies From Synthetic Repertoires of Germline VH Gene Segments Rearranged in vitro," J. Mol. Biol. 227:381-8 (1992); Marks et al., "By-passing Immunization. Human Antibodies from V-gene Libraries Displayed on Phage," J. Mol. Biol. 222: 581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety.

Based on a BLAST search of Genbank using the 4A12 $V_H$ and $V_L$ domain nucleotide sequences, homologous sequences within the human genome were identified as IgKV1-27*02 and IgKJ4*02 for the $V_L$ domain, and IgHV1-46*03 and IgHJ6*02 for the $V_H$ domain.

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988); Houston et al., "Protein Engineering of Antibody Binding Sites: Recovery of Specific Activity in an Anti-Digoxin Single-Chain Fv Analogue Produced in Escherichia coli," Proc. Natl. Acad. Sci. USA 85:5879-5883 (1988); Bird et al, "Single-Chain Antigen-Binding Proteins," Science 242:423-426 (1988), which are hereby incorporated by reference in their entirety, or other methods known in the art.

It may further be desirable, especially in the case of antibody fragments, to modify the antibody to increase its serum half-life. This can be achieved, for example, by incorporation of a salvage receptor binding epitope into the antibody fragment by mutation of the appropriate region in the antibody fragment or by incorporating the epitope binding site into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," J. Mol. Biol. 284:1141-1151 (1998); Koide et al., "Probing Protein Conformational Changes in Living Cells by Using Designer Binding Proteins: Application to the Estrogen Receptor," Proc. Natl. Acad. Sci. USA 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," Nature Biotechnol. 15(8):772-777 (1997), which is hereby incorporated by reference in its entirety).

In preparing these antibody mimics the CDR sequences of the $V_H$ and/or $V_L$ chains can be grafted into the variable loop regions of these antibody mimics. The grafting can involve a deletion of at least two amino acid residues up to substantially all but one amino acid residue appearing in a particular loop region along with the substitution of the CDR sequence. Insertions can be, for example, an insertion of the CDR domain at one or more locations of a particular loop region. The antibody mimics of the present invention preferably possess an amino acid sequence which is at least 50% homologous to the $V_H$ and/or $V_L$ chains sequences disclosed in the present application. The deletions, insertions, and replacements on the polypeptides can be achieved using recombinant techniques beginning with a known nucleotide sequence (see infra).

Methods for monoclonal antibody production may be achieved using the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., S. aureus glucosaminidase or peptide fragments thereof).

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," Eur. J. Immunol. 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Thus, a second aspect of present invention relates to a cell line that expresses a monoclonal antibody of the present invention. In one embodiment the monoclonal antibody of the present invention is produced by a hybridoma cell line designated as 4A12. In another embodiment, the monoclonal antibody of the present invention (or a binding portion thereof) is produced by a recombinant cell or cell line.

As noted above, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, generate host cells that express and secrete monoclonal antibodies. Also, recombinant monoclonal antibodies or fragments thereof of the desired species can be isolated from phage display libraries (McCafferty et al., "Phage Antibodies: Filamentous Phage Displaying Antibody Variable Domains," Nature 348:552-554 (1990); Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222:581-597 (1991), which are hereby incorporated by reference in their entirety).

The present invention also includes a nucleic acid molecule encoding a polypeptide of the present invention. In one embodiment the nucleic acid is DNA. Examples of such DNA sequences are those that comprise a $V_H$ and/or $V_L$ encoding sequence of the present invention. A DNA sequence encoding for hybridoma 4A12 $V_H$ (closest germ line match: J558.59.155 and JH4) has the nucleotide sequence (SEQ ID NO: 4) as follows:

```
CAGGTCCAACTGCAGCAGCCTGGGGCTGAGCTGGTGGGGCCTG

GGACTTCAGTGAAGTTGTCCTGCAAGTCTTCTGGCTACACCTT

CACCAAGTACTGGATGCACTGGCTAAAGCAGAGGCCTGGACAA

GGCCTTGAGTGGATCGGAGTGATTGATCCTTCTGATAGTTATA

CTAACTACAATCAAAAGTTCAAGGGCAAGGCCACATTGACTGT

AGACACATCCTCCAGCACAGCCTACCTGCAGCTCAGCAGCCTG

ACATCTGAGGACTCTGCGGTCTATTACTGTGCCAATTACTACG

GTAGTTACTACGACGTTATGGACTTCTGGGGTCAAGGAACCTC

AGTCACCGTCTCCTCA
```

A DNA sequence encoding for the 4A12 $V_L$ (closest germ line match: RF and JK5) has the nucleotide sequence (SEQ ID NO: 5) as follows:

```
GATGTCCAGATAACCCAGTCTCCATCTTATCTTGCTGCATCTC

CTGGAGAGACCATTACTATTAATTGCAGGGCAAGTAAGAGCAT
```

```
            TAGCAAATATTTAGCCTGGTATCAAGAGAAACCTGGGAAAACG

AATAAGCTTCTTATCTGCTTTGGATCCACTTTGCAATCTGGAA

CTCCATCAAGGTTCAGTGGCAGTGGATCTGGTACAGATTTCAC

TCTCACCATCAGTAGCCTGGAGCCTGAAGATTTTGCAACGTAT

TACTGTCAACAGCATAATGAATACCCGCTCACGTTCGGTGCTG

GGACCAAGCTGGAGCTGAAACGT
```

Still a further aspect of the present invention is a DNA construct comprising a DNA molecule that encodes an antibody or binding portion of the present invention, a promoter-effective DNA molecule operably coupled 5' of the DNA molecule, and a transcription termination DNA molecule operably coupled 3' of the DNA molecule. The present invention also encompasses an expression vector into which the DNA construct of the present invention is inserted. A synthetic gene for the polypeptides of the present invention can be designed such that it includes convenient restriction sites for ease of mutagenesis and uses specific codons for high-level protein expression (Gribskov et al., "The Codon Preference Plot: Graphic Analysis of Protein Coding Sequences and Prediction of Gene Expression," Nucl. Acids. Res. 12:539-549 (1984), which is hereby incorporated by reference in its entirety).

The gene may be assembled as follows: first the gene sequence can be divided into parts with boundaries at designed restriction sites; for each part, a pair of oligonucleotides that code opposite strands and have complementary overlaps of about 15 bases can be synthesized; the two oligonucleotides can be annealed and single strand regions can be filled in using the Klenow fragment of DNA polymerase; the double-stranded oligonucleotide can be cloned into a vector, such as, the pET3a vector (Novagen) using restriction enzyme sites at the termini of the fragment and its sequence can be confirmed by a DNA sequencer; and these steps can be repeated for each of the parts to obtain the whole gene. This approach takes more time to assemble a gene than the one-step polymerase chain reaction (PCR) method (Sandhu et al., "Dual Asymetric PCR: One-Step Construction of Synthetic Genes," BioTech. 12:14-16 (1992), which is hereby incorporated by reference in its entirety). Mutations could likely be introduced by the low fidelity replication by Taq polymerase and would require time-consuming gene-editing. Recombinant DNA manipulations can be performed according to SAMBROOK & RUSSELL, MOLECULAR CLONING: A LABORATORY MANUAL (2d ed. 1989), which is hereby incorporated by reference in its entirety, unless otherwise stated. To avoid the introduction of mutations during one-step PCR, high fidelity/low error polymerases can be employed as is known in the art.

Desired mutations can be introduced to the polypeptides sequence of the present invention using either cassette mutagenesis, oligonucleotide site-directed mutagenesis techniques (Deng & Nickoloff, "Site-Directed Mutagenesis of Virtually any Plasmid by Eliminating a Unique Site," Anal. Biochem. 200:81-88 (1992), which is hereby incorporated by reference in its entirety), or Kunkel mutagenesis (Kunkel et al., "Rapid and Efficient Site-Specific Mutagenesis Without Phenotypic Selection," Proc. Natl. Acad. Sci. USA 82:488-492 (1985); Kunkel et al., "Rapid and Efficient Site-Specific Mutagenesis Without Phenotypic Selection," Methods Enzymol. 154:367-382 (1987), which are hereby incorporated by reference in their entirety).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis. Regardless of the approach utilized to introduce mutations into the nucleotide sequence encoding a polypeptide according to the present invention, sequencing can be performed to confirm that the designed mutations (and no other mutations) were introduced by mutagenesis reactions.

In contrast, Kunkel mutagenesis can be utilized to randomly produce a plurality of mutated polypeptide coding sequences which can be used to prepare a combinatorial library of polypeptides for screening. Basically, targeted loop regions (or C-terminal or N-terminal tail regions) can be randomized using the NNK codon (N denoting a mixture of A, T, G, C, and K denoting a mixture of G and T) (Kunkel et al., "Rapid and Efficient Site-Specific Mutagenesis Without Phenotypic Selection," Methods Enzymol. 154:367-382 (1987), which is hereby incorporated by reference in its entirety).

Regardless of the approach used to prepare the nucleic acid molecules encoding the polypeptide according to the present invention, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the polypeptide and a transcription termination (i.e., polyadenylation sequence) can be operably coupled 3' thereof.

In accordance with this aspect of the invention, the polynucleotides of the present invention are inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if E. coli is used as a host cell, plasmids such as pUC19, pUC18 or pBR322 may be used. When using insect host cells, appropriate transfer vectors compatible with insect host cells include, pVL1392, pVL1393, pAcGP67 and pAcSecG2T, which incorporate a secretory signal fused to the desired protein, and pAcGHLT and pAcHLT, which contain GST and 6× His tags (BD Biosciences, Franklin Lakes, N.J.). Viral vectors suitable for use in carrying out this aspect of the invention include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of antibodies or antibody fragments that are produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, 1 pp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR. The promoters can be constitutive or, alternatively, tissue-specific or inducible. In addition, in some circumstances inducible (Teton) promoters can be used.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination In Vitro," *Methods in Enzymology*, 68:473-82 (1979), which is hereby incorporated by reference in its entirety.

The present invention also includes a host cell transformed with the DNA construct of the present invention. The host cell can be a prokaryote or a eukaryote. Host cells suitable for expressing the polypeptides of the present invention include any one of the more commonly available gram negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N meningitides, Haemophilus influenzae, H. pleuropneumoniae, Pasteurella haemolytica, P. multilocida, Legionella pneumophila, Treponema pallidum, T denticola, T. orales, Borrelia burgdorferi, Borrelia* spp., *Leptospira interrogans, Klebsiella pneumoniae, Proteus vulgaris, P. morganii, P. mirabilis, Rickettsia prowazeki, R. typhi, R. richettsii, Porphyromonas (Bacteriodes) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida,* and *Yersinia pestis*.

In addition to bacteria cells, animal cells, in particular mammalian and insect cells, yeast cells, fungal cells, plant cells, or algal cells are also suitable host cells for transfection/transformation of the recombinant expression vector carrying an isolated polynucleotide molecule of the present invention. Mammalian cell lines commonly used in the art include Chinese hamster ovary cells, HeLa cells, baby hamster kidney cells, COS cells, and many others. Suitable insect cell lines include those susceptible to baculoviral infection, including Sf9 and Sf21 cells.

Methods for transforming/transfecting host cells with expression vectors are well-known in the art and depend on the host system selected, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage. For eukaryotic cells, suitable techniques include calcium phosphate transfection, DEAE-Dextran, electroporation, liposome-mediated transfection, and transduction using retrovirus or any other viral vector. For insect cells, the transfer vector containing the polynucleotide construct of the present invention is co-transfected with baculovirus DNA, such as AcNPV, to facilitate the production of a recombinant virus. Subsequent recombinant viral infection of Sf cells results in a high rate of recombinant protein production. Regardless of the expression system and host cell used to facilitate protein production, the expressed antibodies, antibody fragments, or antibody mimics of the present invention can be readily purified using standard purification methods known in the art and described in PHILIP L. R. BONNER, PROTEIN PURIFICATION (Routledge 2007), which is hereby incorporated by reference in its entirety.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a humanized (or chimeric) antibody, as discussed above. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

A further aspect of the present invention is related to a pharmaceutical composition comprising a carrier and one or more monoclonal antibodies or one or more binding portions thereof in accordance with the present invention. This pharmaceutical composition may contain two or more antibodies or binding fragments where all antibodies or binding fragments recognize the same epitope. Alternatively, the pharmaceutical composition may contain an antibody or binding fragment mixture where one or more antibodies or binding fragments recognize one epitope of *S. aureus* Gmd and one or more antibodies or binding fragments recognize a different epitope of *S. aureus* Gmd. For example, the mixture may contain one or more antibodies of the present invention that bind specifically to an R3 domain of *Staphylococcus aureus* glucosaminidase in combination with any other antibody that binds to glucosaminidase, such as an antibody that binds to the catalytic domain of glucosaminidase. The pharmaceutical composition of the present invention further contains a pharmaceutically acceptable carrier or other pharmaceutically acceptable components as described infra.

In accordance with one embodiment, the pharmaceutical composition includes antibody 4A12, binding fragments thereof, or a chimeric variant thereof in a pharmaceutically acceptable carrier.

In another embodiment, the pharmaceutical composition further includes one or more of mAbs 1C11, 2D11, 3H6, 1E12, and 3A8, binding fragments thereof, or chimeric variants thereof.

A pharmaceutical composition containing the antibodies of the present invention can be administered to a subject having or at risk of having *Staphylococcus* infection. Various delivery systems are known and can be used to administer the antibodies of the present invention. Methods of introduction include but are not limited to intradermal, intramuscular, intraperitoneal, intravenous, subcutaneous, intranasal, epidural, and oral routes. The therapeutic agent can be administered, for example by infusion or bolus injection, by absorption through epithelial or mucocutaneous linings (e.g., oral mucosa, rectal and intestinal mucosa, and the like) and can be administered together with other biologically active agents, such as chemotherapeutic agents, antibiotic agents, or other immunotherapeutic agents. Administration can be systemic or local, i.e., at a site of Staph infection or directly to a surgical or implant site.

The pharmaceutical composition of the present invention can further comprise administering a second therapeutic agent to the patient, wherein the second therapeutic agent is an antibiotic agent or immunotherapeutic agent. Exemplary antibiotic agents include, without limitation, vancomycin, tobramycin, cefazolin, erythromycin, clindamycin, rifampin, gentamycin, fusidic acid, minocycline, co-trimoxazole, clindamycin, linezolid, quinupristin-dalfopristin, daptomycin, tigecycline, dalbavancin, telavancin, oritavancin, ceftobiprole, ceftaroline, iclaprim, the carbapenem CS-023/RO-4908463, and combinations thereof. Exemplary immunotherapeutic agents include, without limitation, tefibazumab, BSYX-A110, Aurexis™, and combinations thereof. The above lists of antibiotic agents and immunotherapeutic agents are intended to be non-limiting examples; thus, other antibiotic agents or immunotherapeutic agents are also contemplated. Combinations or mixtures of the second therapeutic agent can also be used for the purposes of the present invention. These agents can be administered contemporaneously or as a single formulation.

The pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

Effective doses of the compositions of the present invention, for the treatment of the above described bacterial infections vary depending upon many different factors, including mode of administration, target site, physiological state of the patient, other medications administered, and whether treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. For prophylactic treatment against *Staphylococcus* bacterial infection, it is intended that the pharmaceutical composition(s) of the present invention can be administered prior to exposure of an individual to the bacteria and that the resulting immune response can inhibit or reduce the severity of the bacterial infection such that the bacteria can be eliminated from the individual. For example, the monoclonal antibody or the pharmaceutical composition can be administered prior to, during, and/or immediately following a surgical procedure, such as joint replacement or any surgery involving a prosthetic implant.

For passive immunization with an antibody or binding fragment of the present invention, the dosage ranges from about 0.0001 to about 100 mg/kg, and more usually about 0.01 to about 5 mg/kg, of the host body weight. For example, dosages can be about 1 mg/kg body weight or about 10 mg/kg body weight, or within the range of about 1 to about 10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be daily, weekly, monthly, or yearly. In some methods, dosage is adjusted to achieve a plasma antibody concentration of 1-1000 mg/ml and in some methods 25-300 mg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies.

Another aspect the present invention relates to a method of treating an *S. aureus* infection that includes administering to a patient having an *S. aureus* infection an effective amount of a monoclonal antibody or binding fragment thereof or a pharmaceutical composition of the present invention.

In one embodiment of this aspect of the invention the method of treating *S. aureus* infection further comprises repeating said administering. The method of treating *S. aureus* infection can be such that the administering is carried out systemically or carried out directly to a site of the *S. aureus* infection.

The method of treating *S. aureus* infection can be used to treat *S. aureus* infection at sites which include, without limitation, infection of the skin, muscle, cardiac, respiratory tract, gastrointestinal tract, eye, kidney and urinary tract, and bone or joint infections.

In one embodiment, this method is carried out to treat osteomyelitis by administering an effective amount of the monoclonal antibody or binding fragment thereof or the pharmaceutical composition of the present invention to a patient having an *S. aureus* bone or joint infection. Administration of these agents or compositions can be carried out using any of the routes described supra; however, administration directly to the site of the bone or joint infection is preferred.

A further aspect of the present invention relates to a method of introducing an orthopedic implant into a patient that includes administering to a patient in need of an orthopedic implant an effective amount of a monoclonal antibody, binding portion, or pharmaceutical composition of the present invention, and introducing the orthopedic implant into the patient.

In one embodiment, the method of introducing an orthopedic implant includes administering to the patient in need of the orthopedic implant an effective amount of a monoclonal antibody or binding fragment or a pharmaceutical composition containing the same, directly to the site of implantation. Alternatively, or in addition, the orthopedic implant can be coated or treated with the monoclonal antibody or binding fragment or a pharmaceutical composition containing the same before, during, or immediately after implantation thereof at the implant site.

The orthopedic implant can be a joint prosthesis, graft or synthetic implant. Exemplary joint prosthetics includes, without limitation, a knee prosthetic, hip prosthetic, finger prosthetic, elbow prosthetic, shoulder prosthetic, temperomandibular prosthetic, and ankle prosthetic. Other prosthetics can also be used. Exemplary grafts or synthetic implants include, without limitation, an artificial intervertebral disk, meniscal implant, or a synthetic or allograft anterior cruciate ligament, medial collateral ligament, lateral collateral ligament, posterior cruciate ligament, Achilles tendon, and rotator cuff Other grafts or implants can also be used.

In one embodiment, the method of introducing an orthopedic implant is intended to encompass the process of installing a revision total joint replacement. Where infection, particularly Staph infection of an original joint replacement occurs, the only viable treatment is a revision total joint replacement. In this embodiment, the infected joint prosthesis is first removed and then the patient is treated for the underlying infection. Treatment of the infection occurs over an extended period of time (i.e. 6 months), during which time the patient is immobile (or has only limited mobility) and receives high doses of antibiotics to treat the underlying infection and optionally one or more monoclonal antibodies or binding portions, or pharmaceutical compositions of the present invention. Upon treatment of the underlying infection, the new joint prosthesis is installed. Immediately prior (i.e., within the two weeks preceding new joint prosthesis installation) and optionally subsequent to installation of the new joint prosthesis, the patient is administered one or more monoclonal antibodies or binding portions, or pharmaceutical compositions of the present invention. This treatment can be repeated one or more times during the post-installation period. Antibiotic treatment may be administered in combination with or concurrently with the one or more monoclonal antibodies or binding portions, or pharmaceutical compositions of the present invention. These treatments are effective to prevent infection or reinfection during the revision total joint replacement.

The methods of treatment according to the present invention can be used to treat any patient in need, however, the methods are particularly useful for immuno-compromised patients of any age, as well as patients that are older than 50 years of age.

Another aspect of the present invention relates to a method of assessing immunity of an individual against *S. aureus* including exposing an *S. aureus* glucosaminidase (Gmd) to a substrate of the Gmd in the presence of sera from the individual and assessing the activity of the Gmd on the substrate after said exposing. This method is particularly useful for assessing the need of a patient to receive an antibody of the present invention or a fragment thereof for therapeutic or prophylactic treatment.

In one embodiment, the method is carried out using a Gmd from a methicillin resistant *S. aureus* as described above.

The substrate of the Gmd can be any suitable substrate of the enzyme. One exemplary substrate is an *M. luteus* cell wall preparation. The term "cell wall" as used herein describes all components forming the outer cell envelope of the bacteria and thus guarantees their integrity. Methods for purifying bacterial cell walls are well known in the art and include, but are not limited to, preparation of native walls and SDS-walls. Native cell walls are prepared from exponential-phase cultures that are pelleted by centrifugation. The bacteria are then resuspended in buffer and disrupted by ultrasonic oscillation. Removal of undisrupted bacteria is performed with slow speed centrifugation followed by collection of the supernatant containing the cell walls (Fein and Rogers, "Autolytic Enzyme-Deficient Mutants of *Bacillus subtilis* 168," *J Bacteriol.* 127(13): 1427-1442 (1976), which is hereby incorporated by reference in its entirety).

SDS-treated cell walls can be prepared from feeeze dried cells or cells grown into the exponential phase as described by Fein and Rogers, "Autolytic Enzyme-Deficient Mutants of *Bacillus subtilis* 168," *J. Bacteriol.* 127(13): 1427-1442, which is hereby incorporated by reference in its entirety.

In accordance with this aspect of the present invention, assessing immunity of an individual against *S. aureus* can be carried out by measuring the absorbance, using a spectrophotometer, of the bacterial cell wall suspension after exposure to Gmd in both the presence and absence of sera from said individual, followed by analyzing the ability of the sera to inhibit the cell wall lytic activity of the Gmd. The sera can be diluted in a salt solution acceptable in the art and contacted with about 1 mg/ml of purified Gmd in a microtiter plate for 60 minutes at 37° C. The absorbance of the sample can then be read at 490 nm on a spectrophotometer. This immune status of the individual can be determined according to the equation: % Inhibition=100(1-(change in absorbance measured in the presence of sera after 60 minutes/change in absorbance measured in the absence of sera after 60 minutes)). In this analysis, the decrease in light scattering of the bacterial suspension is correlated to the amount of lytic enzyme (i.e. Gmd) functioning to lyse the bacterial cell wall, and the presence of immunity to Gmd is reflected by the ability of sera to inhibit cell wall lysis by Gmd.

The sera from the individual can be freshly isolated sera or it can be thawed frozen sera. Regardless, the sera can be diluted at about 1:10 to about 1:1000, as desired, prior to using the sera in the assay. Methods well known in the art can be used to isolate sera from the blood of an individual.

As described above, the exposing and assessing steps can be carried out in parallel with a negative control (i.e., buffer solution containing no sera). These steps can alternatively be carried out in parallel with a positive control, such as a solution containing one or more monoclonal antibodies or binding fragments of the present invention (preferably at a concentration that will result in at least 50% inhibition of Gmd activity). In a further embodiment, both the positive and negative controls are used in parallel with the sera of the individual. In certain embodiments, the monoclonal anti-Gmd antibody is 4A12, 1C11, 2D11, 3H6, 1E12, or 3A8, or a binding fragment thereof.

EXAMPLES

The present invention is illustrated by reference to the following examples. These examples are not intended to limit the claimed invention.

Example 1

A Murine Transtibial Model of Implant-Associated Osteomyelitis

Figure 1A:
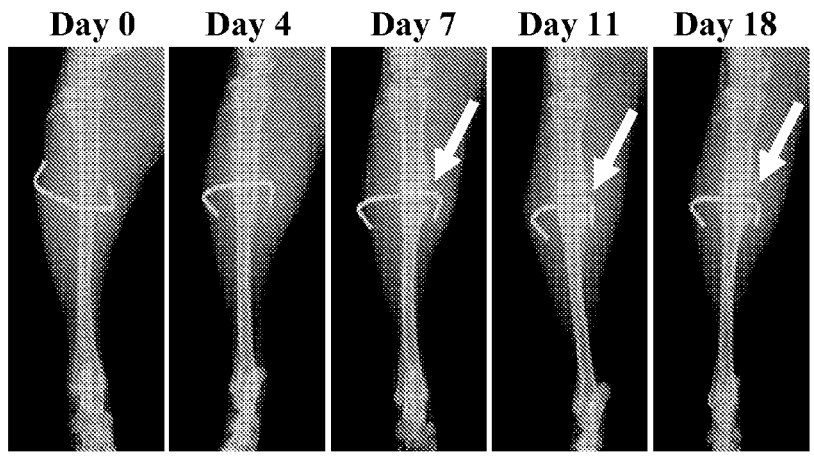
FIGS. 1A-C show the quantification of osteolysis from implant-associated osteomyelitis. A longitudinal series of X-rays from a representative mouse demonstrate the development of implant-associated osteolysis over time in this model (FIG. 1A). Medial views of reconstructed μCET (micro-computed tomography) images of representative tibiae from mice (N=5) that received a trans-tibial pin coated with S. aureus and were sacrificed on the indicated day (FIG.

Orthopedic implant-associated OM occurs for both intramedullary devices (i.e. joint prostheses) and transcortical implants (i.e. external fixation devices, FIG. 1A). Although the infection rate of fixation devices is 2.5 times greater, and has an incidence of over 8-times that of total joint prostheses, it is not considered to be as serious because the revision surgery is much simpler (Darouiche, "Treatment of Infections Associated With Surgical Implants," *N. Engl. J. Med.* 350(14):1422-9 (2004), which is hereby incorporated by reference in its entirety). While most cases involving an infected transcortical implant can be resolved in a single surgery to relocate the pin and treating the abscess independently, the majority of infected prostheses must undergo two revision surgeries (Darouiche, "Treatment of Infections Associated With Surgical Implants," *N. Engl. J. Med.* 350 (14):1422-9 (2004), which is hereby incorporated by reference in its entirety). The first is needed to cure the infection, and the second replaces the prosthesis. Thus, from a clinical significance standpoint, the field has focused primarily on models of implant-associated OM that involve an intramedullary device with the UAMS-1 (ATCC 49230) strain of *S. aureus* (Daum et al., "A Model of *Staphylococcus aureus* Bacteremia, Septic Arthritis, and Osteomyelitis in Chickens," *J. Orthop. Res.* 8(6):804-13 (1990); Rissing et al., "Model of Experimental Chronic Osteomyelitis in Rats," *Infect. Immun.* 47(3):581-6 (1985); Passl et al., "A Model of Experimental Post-Traumatic Osteomyelitis in Guinea Pigs," *J. Trauma* 24(4):323-6 (1984); Worlock et al., "An Experimental Model of Post-Traumatic Osteomyelitis in Rabbits," *Br. J. Exp. Pathol.* 69(2):235-44 (1988); Varshney et al., "Experimental Model of Staphylococcal Osteomyelitis in Dogs," *Indian J. Exp. Biol.* 27(9):816-9 (1989); Kaarsemaker et al., "New Model for Chronic Osteomyelitis With *Staphylococcus aureus* in Sheep," *Clin. Orthop. Relat. Res.* 339:246-52 (1997), which are hereby incorporated by reference in their entirety). Unfortunately, this approach has significant limitations, most notably the inability to generate reproducible (temporal and spatial) lesions. In an effort to overcome this the location of the infection was guided to the diaphysis by fracturing the tibia immediately after inserting an intramedullary pin containing $1\times10^6$ CFU, using an Einhorn device as described previously (Zhang et al., "Cyclooxygenase-2 Regulates Mesenchymal Cell Differentiation Into the Osteoblast Lineage and is Critically Involved in Bone Repair," *J. Clin. Invest.* 109(11):1405-15 (2002), which is hereby incorporated by reference in its entirety). It was found that implantation of an infected transcortical pin always produces lesions adjacent to the pin, and never results in chronic OM in other regions of the tibia or hematogenous spreading in mice (FIGS. 1A-C).

Figure 1B:
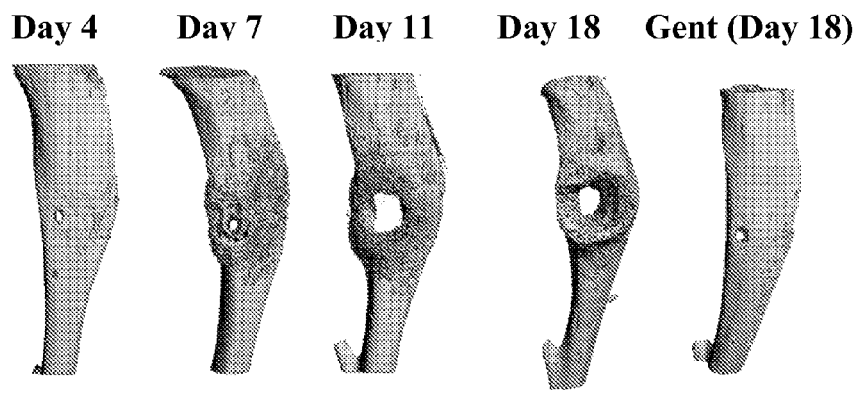
Figure 1C:
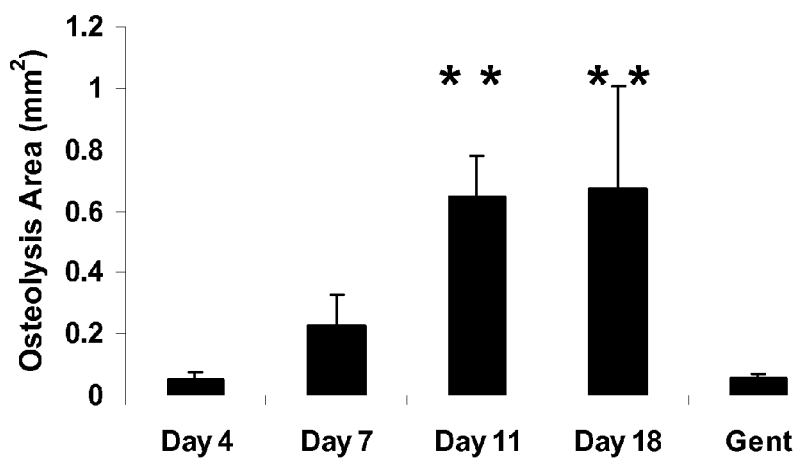

To quantify the osteolysis, a time-course study was performed in which the infected tibiae were analyzed by μCT (FIGS. 1B-C). These results are consistent with sequestrum formation in which osteoclastic bone resorption around the infected implant occurs with concomitant reactive periosteal bone formation.

The presence of OM in the mice was confirmed histologically. FIGS. 2A-H demonstrate that the tibial transcortical pin model contains all of the salient features of chronic OM including: sequestrum and involucrum formation, osteoclastic resorption of the cortical bone and Gram stained extracellular bacteria and biofilm that reside in the necrotic bone surrounding the implant. None of the negative controls, including heat killed *S. aureus* and non-pathogenic *E. coli*, demonstrated these features.

Example 2

Real Time PCR Quantitation of Osteomyelitis

There are no known methods to quantify OM. Since it is impossible to effectively extract live bacteria from infected bone to determine bacterial load by classical colony forming units (CFU), a real time PCR method was developed to quantify the number of recoverable nuc genes in DNA samples, as is done to test for contamination in cheese (Hein et al., "Comparison of Different Approaches to Quantify *Staphylococcus aureus* Cells by Real-Time Quantitative PCR and Application of This Technique for Examination of Cheese," *Appl. Environ. Microbiol.* 67(7):3122-6 (2001), which is hereby incorporated by reference in its entirety) and blood (Palomares et al., "Rapid Detection and Identification of *Staphylococcus aureus* From Blood Culture Specimens Using Real-Time Fluorescence PCR," *Diagn. Microbiol. Infect. Dis.* 45(3):183-9 (2003), which is hereby incorporated by reference in its entirety), as a surrogate outcome measure of bacterial load.

RTQ-PCR for the *S. aureus*-specific nuc gene can be performed using primers 5'-GCGATTGATGGTGATACG-GTT-3' (SEQ ID NO: 6) and 5'-AGCCAAGCCTTGAC-GAACTAA-3' (SEQ ID NO: 7) that amplify a previously described 269-bp product (Hein et al., "Comparison of Different Approaches to Quantify *Staphylococcus aureus* Cells by Real-Time Quantitative PCR and Application of This Technique for Examination of Cheese," *Appl. Environ. Microbiol.* 67(7):3122-6 (2001), which is hereby incorporated by reference in its entirety). The reactions can be carried out in a final volume of 20 µl consisting of 0.3 µM primers, 1× Sybr Green PCR Super Mix (BioRad, Hercules, Calif.), and 2 µM of the purified tibia DNA template. The samples can be assayed using a Rotor-Gene RG 3000 (Corbett Research, Sydney, AU).

To control for the integrity of the DNA template between samples, RTQ-PCR can also be performed for the mouse β-actin gene that detects a 124-bp product using primers 5'-AGATGTGAATCAGCAAGCAG-3' (SEQ ID NO: 8) and 5'-GCGCAAGTTAGGTTTTGTCA-3' (SEQ ID NO: 9). Using PCR primers specific for murine β-actin, *S. aureus* nuc, and rRNA genomic DNA, the specificity of these PCRs and the ability to amplify the predicted products was demonstrated (Li et al., "Quantitative Mouse Model of Implant-Associated Osteomyelitis and the Kinetics of Microbial Growth, Osteolysis, and Humoral Immunity," *J. Orthop. Res.* 26(1):96-105 (2008), which is hereby incorporated by reference in its entirety). Then, using purified plasmid DNA containing the nuc gene, or *S. aureus* genomic DNA, a dose response experiment was performed and it was determined that the detection limit for this RTQ-PCR is ~100 copies (Li et al., "Quantitative Mouse Model of Implant-Associated Osteomyelitis and the Kinetics of Microbial Growth, Osteolysis, and Humoral Immunity," *J. Orthop. Res.* 26(1): 96-105 (2008), which is hereby incorporated by reference in its entirety). This assay has been used to quantify the in vivo bacterial load as a secondary outcome measure of infection and efficacy of the passive immunization.

Example 3

Kinetics of Infection and Humoral Immunity During the Establishment of Osteomyelitis To quantify microbial pathogenesis and host immunity during the establishment of osteomyelitis, a time course study was performed in which mice were given an infected transcortical pin implant in their tibia, and the bacterial load and the host humoral response was determined over time by nuc/β-actin RTQ-PCR and western blot, respectively (FIGS. 3A-C). The results indicate a clear inverse correlation between infection and humoral immunity. Consistent with classical microbial pathogenesis and acquired immunity to extracellular bacteria, these results indicate that the bacteria immediately establish themselves and enter an exponential growth phase, which is extinguished by a neutralizing humoral response after 11 days. Based on the coincidence of the peak bacterial load with the genesis of high affinity IgG antibodies against specific bacterial proteins, it is evident that these "immuno-dominant" antigens elicit a functional immune response that is both diagnostic and protective against the establishment of OM.

Example 4

Identification and Cloning of the Glucosaminidase Subunit of *S. aureus* Autolysin as 56 kDa Immuno-Dominant Antigen that Elicits a Specific IgG2b Response During the Establishment of OM To further characterize the humoral response during the establishment of OM, the prevalence of Ig isotypes in the serum of mice was determined over the first two weeks of infection by ELISA (Li et al., "Quantitative Mouse Model of Implant-Associated Osteomyelitis and the Kinetics of Microbial Growth, Osteolysis, and Humoral Immunity," *J. Orthop. Res.* 26(1):96-105 (2008), which is hereby incorporated by reference in its entirety). The results showed that the mice initiate a classical IgM response in the first week that converts to a specific IgG2b response in the second week, which has recently been shown to have potent opsonic and protective activities against *S. aureus* antigens (Maira-Litran et al., "Comparative Opsonic and Protective Activities of *Staphylococcus aureus* Conjugate Vaccines Containing Native or Deacetylated Staphylococcal Poly-N-acetyl-beta-(1-6)-glucosamine," *Infect. Immun.* 73(10):6752-62 (2005), which is hereby incorporated by reference in its entirety).

To elucidate the molecular identity of the immuno-dominant antigens identified in FIG. 3C, subtractive Western blotting of total *S. aureus* extract was performed that was separated by 2D-PAGE (FIGS. 4A-C). This analysis revealed a polypeptide that was not detected by the pre-immune serum, but had strong reactivity with the day 14 post-immune serum. The protein was isolated from a preparative Coomassie blue stained gel, digested with trypsin, and analyzed by matrix-assisted laser desorption/ionization (MALDI), which resolved 70 individual peptide peaks. The amino acid sequence from every peptide was a 100% match with the known sequence of the Gmd subunit of *S. aureus* Alt. Interestingly, others have also recently found Atl to be an immuno-dominant antigen in a rabbit tibia model of MRSA OM (Brady et al., "Identification of *Staphylococcus aureus* Proteins Recognized by the Antibody-Mediated Immune Response to a Biofilm Infection," Infect. Immun. 74(6):3415-26 (2006), which is hereby incorporated by reference in its entirety).

To confirm that the spot picked from the 2D-PAGE gel in FIG. 4C was the relevant immuno-dominant antigen, a recombinant 6-His tagged fusion protein was generated by cloning the 1,465 bp coding region of the 53 kDa glucosaminidase subunit of *S. aureus* autolysin into the XhoI-BamHI site of the pET-28a(+) expression plasmid (Novagen), which contains the lac I promoter for IPTG induction. Following DNA sequencing, the plasmid was used to transform BL21 *E. coli*, which were used to make recombinant His-glucosaminidase (His-Gmd). This recombinant protein was then used to evaluate the reactivity of pre-immune and immune sera. The results showed that the IPTG induced 57 kDa recombinant protein is only recognized by immune serum, thus confirming that Gmd is a *S. aureus* immuno-dominant antigen. This experiment was repeated with anti-sera from mice infected with Xen 29, and confirmed that C57Bl/6 also generate Gmd specific antibodies against this bioluminescent strain of *S. aureus*.

Example 5

In Vivo Bioluminescence Imaging of Lux Transformed S. aureus as a Longitudinal Outcome Measure of OM and Bacterial Growth Although the RTQ-PCR method of quantifying OM in mouse model is very useful, there are three major limitations to this approach. First, it is not longitudinal, as analysis requires sacrifice of the mice to harvest the DNA. Second, it is very labor intense and requires great care during the DNA isolation, PCR and data analysis. Third, detection of S. aureus genomic DNA (nuc genes) cannot distinguish between bacteria that are in an active growth phase vs. dormant bacteria tightly packed in a biofilm. Thus, RTQ-PCR cannot be readily used to assess mAb effect on bacterial growth in vivo.

To overcome these shortcomings, the present invention relates to a highly innovative approach to monitor pathogens in vivo using bioluminescence imaging (Contag et al., "Photonic Detection of Bacterial Pathogens in Living Hosts," Mol. Microbiol. 18(4):593-603 (1995), which is hereby incorporated by reference in its entirety). More recently, P. R. Contag and colleagues have generated bioluminescent S. aureus (Xen 29; ATCC 12600) for this purpose (Francis et al., "Monitoring Bioluminescent Staphylococcus aureus Infections in Living Mice Using a Novel luxABCDE Construct," Infect. Immun. 68(6):3594-600 (2000), which is hereby incorporated by reference in its entirety). FIGS. 5A-B demonstrate how this approach is adapted in the model of OM of the present invention. In a time-course studies with Xen29, only background signal was detected in mice that received a sterile pin or infected mice treated with parenteral gentamycin. In contrast, the BLI of infected, untreated tibiae demonstrated a sharp 4-fold increase from baseline on day 4, which subsequently dropped to background levels by day 11.

Example 6

Recombinant Gmd Vaccine Protects Mice from Implant-Associated OM

To assess the potential of an anti-autolysin passive immunization for OM, an initial active recombinant Gmd vaccine study was performed in which mice (n=20) were immunized as follows: Group 1 (PBS in adjuvant (negative control)); Group 2 (20 µg S. aureus Xen 29 total proteome extract emulsified 1:1 with equal volume of adjuvant (positive control)); Group 3 (20 µg His-glucosaminidase in adjuvant). A 150 µl emulsion of each vaccine was injected intramuscularly (i.m.) 28 day prior to challenge. Booster immunizations (i.m.; 20 µg protein in Freund's incomplete adjuvant) were performed 14 days prior to challenge.

To assess the vaccine efficacy in these mice, an anti-Gmd ELISA was developed (FIG. 6A) and used to quantify serum antibody titers before initial immunization, before booster immunization, and before the bacterial challenge (FIG. 6B). Remarkably, the results demonstrated that only the recombinant vaccine elicited a high titer immune response. To assess the efficacy of these vaccines, the immunized mice were challenged with a Xen29 infected transtibial pin as described in the preceding Example (see FIG. 5A-C), BLI was performed on day 3, and the mice were euthanized for nuc RTQ-PCR on day 11. Remarkably, 18 out of the 20 mice immunized with S. aureus total proteome died within 48 hr of the challenge; thus efficacy data from that group are not available. While only speculative explanations can be provided for this observation (i.e. hyper-immunity to other antigens), the fact that no death occurred in any of the other groups and that the deaths were reproduced in the 4 cohorts of 5 mice in Group 2 indicates that the results are real. For this reason, this immunization protocol should not be used as a positive control for future studies. It also highlights the safety concerns with active vaccines, and supports the rationale of a passive immunization with purified mAb or binding fragments thereof.

The BLI and nuc RTQ-PCR data from Groups 1 and 3 are presented in FIGS. 7A-C. The results clearly demonstrate a significant reduction of BLI detected in the His-Gmd immunized mice (FIGS. 7A-B), which shows a decrease in planktonic growth of the bacteria. Consistent with this finding, it was observed that there was a significant reduction in the number of nuc genes at the peak of the bacterial load in this model (day 11). Thus, these data demonstrate that the recombinant Gmd vaccine can protect mice from OM in the model.

Example 7

Generation and Screening of Mouse Anti-Gmd Monoclonal Antibodies

Based on the success of the His-Gmd immunization described in Example 6, this protocol was used to generate mouse anti-Gmd mAb. Standard procedures were used to generate the mAb. Out of an initial pool of hybridomas that were prepared, a first subset was selected following screened by ELISA for anti-Gmd activity and a second subset possessing higher affinity were selected following a western dot-blot assay.

Five of the hybridoma cell lines were selected based on their apparent high affinity for Gmd ($\leq 10^{-9}$M) and the putative epitope for these regions being found within the R3 domain of Gmd. Because the R3 domain is not the catalytic domain of the Gmd protein, it was unexpected that these monoclonal antibodies would possess as significant anti-Gmd inhibitory activity. The five selected hybridomas were 1C11, 1E12, 2D11, 3A8 and 3H6. All secreted mouse IgG1 antibodies.

Subsequent to the sequencing and testing of hybridomas 1C11, 1E12, 2D11, 3A8 and 3H6 (described in PCT Application Publication No. WO2011/140114, which is hereby incorporated by reference in its entirety), hybridoma 4A12 was also subjected to sequencing and testing as described below.

Hybridoma 4A12 (Closest germ line matches: J558.59.155 and JH4) has the $V_H$ nucleotide sequence (SEQ ID NO: 4) as follows:

```
CAGGTCCAACTGCAGCAGCCTGGGGCTGAGCTGGTGGGGCCTG

GGACTTCAGTGAAGTTGTCCTGCAAGTCTTCTGGCTACACCTT

CACCAAGTACTGGATGCACTGGCTAAAGCAGAGGCCTGGACAA

GGCCTTGAGTGGATCGGAGTGATTGATCCTTCTGATAGTTATA

CTAACTACAATCAAAAGTTCAAGGGCAAGGCCACATTGACTGT

AGACACATCCTCCAGCACAGCCTACCTGCAGCTCAGCAGCCTG

ACATCTGAGGACTCTGCGGTCTATTACTGTGCCAATTACTACG
```

-continued

```
GTAGTTACTACGACGTTATGGACTTCTGGGGTCAAGGAACCTC

AGTCACCGTCTCCTCA
```

The 4A12 $V_L$ (Closest germ line match: RF and JK5) has the nucleotide sequence (SEQ ID NO: 5) as follows:

```
GATGTCCAGATAACCCAGTCTCCATCTTATCTTGCTGCATCT

CCTGGAGAGACCATTACTATTAATTGCAGGGCAAGTAAGAGC

ATTAGCAAATATTTAGCCTGGTATCAAGAGAAACCTGGGAAA

ACGAATAAGCTTCTTATCTGCTTTGGATCCACTTTGCAATCT

GGAACTCCATCAAGGTTCAGTGGCAGTGGATCTGGTACAGAT

TTCACTCTCACCATCAGTAGCCTGGAGCCTGAAGATTTTGCA

ACGTATTACTGTCAACAGCATAATGAATACCCGCTCACGTTC

GGTGCTGGGACCAAGCTGGAGCTGAAACGT
```

The amino acid sequence of hybridoma 4A12 $V_H$ (SEQ ID NO: 2) is as follows:

```
QVQLQQPGAELVGPGTSVKLSCKSSGYTETKYWMHWLKQRP

GQGLEWIGVIDPSDSYTNYNQKFKGKATLTVDTSSSTAYLQ

LSSLTSEDSAVYYCANYYGSYYDVMDFWGQGTSVTVSS
```

The 4A12 $V_L$ has the amino acid sequence (SEQ ID NO: 3) as follows:

```
DVQITQSPSYLAASPGETITINCRASKSISKYLAWYQEKPG

KTNKLLICFGSTLQSGTPSRFSGSGSGTDFTLTISSLEPED

FATYYCQQHNEYPLTFGAGTKLELKR
```

In comparison to the sequences of the $V_L$ and $V_H$ domains of mAbs 1C11, 1E12, 2D11, 3A8 and 3H6 (described in PCT Application PCT/US2011/035033, which is hereby incorporated by reference in its entirety), the $V_L$ and $V_H$ domains of 4A12 are unique.

Example 8

Inhibition of S. aureus Gmd Enzymatic Activity by mAb 4A12

S. aureus UAMS-1 was grown in 10 mL of LB medium at 37° C. on a rotating platform at 200 rpm for 12 hours to mid-log phase. The bacteria were then diluted in LB medium to 1000 cfu/mL and 100 μL of the diluted suspension was added to wells of a flat-bottomed microtiter (with cover) designated for the addition of the antibodies and controls. Each anti-Gmd and control antibody was diluted into LB from stocks about 1 mg/mL in PBS and sterilized through a 0.2μ filter. 100 μL of each antibody was added to designated quadruplicate wells. Plates were then incubated at 37° C. and light scattering was measured hourly (for 12 hours) at 490 nm on a microtiter plate reader. As shown in FIG. 8, 1C11 and 4A12 displayed comparable in vitro growth inhibition of S. aureus.

Given the results of in vitro growth inhibition, the ability of 4A12 to inhibit S. aureus binary fission was also compared to 1C11, which was previously shown to promote clumping or clustering of S. aureus. S. aureus (Xen29) was cultured in liquid Luria Broth (LB) media in the presence of an irrelevant IgG mAb (CTL), a mAb against S. aureus protein A (Anti-Spa), or 4A12 and 1C11 anti-Gmd mAbs. After 12 hr of culture at 37° C., aliquots of the suspension culture were harvested for scanning electron microscopy. Samples were then plated onto sterile silicon chips, fixed, dehydrated, and coated with gold for visualization by scanning electron microscopy. Representative photographs are presented to illustrate the lack of effects of the CTL and Anti-Spa mAb on binary fission (FIGS. 9A-B, respectively), as the daughter bacteria have clearly defined cell membranes (white arrows). In contrast, both 4A12 (FIG. 9C) and 1C11 (FIG. 9D) inhibit binary fission as evidenced by the extended division plate between the daughter bacteria (red arrows). Evidence of greater inhibition by 4A12 versus 1C11 is provided by the absence of a clearly visible cleavage plate in FIG. 9C.

Example 9

Generation and Testing of Humanized Antibody

The variable regions of the light and heavy chains of the 4A12 antibody were re-amplified from the purified hybridoma PCR product described in Example 7 using primers to permit cloning into the human antibody expression vectors described by Tiller et al. ("Efficient Generation of Monoclonal Antibodies from Single Human B Cells by Single Cell RT-PCR and Expression Vector Cloning," J. Immunol. Methods 329(1-2):112-24 (2008), which is hereby incorporated by reference in its entirety). Plasmids containing the 4A12 light and heavy chain variable regions and human kappa and IgG1 constant regions were prepared and co-transfected into HEK293 cells. After 3 days, the medium was removed from the cells and assayed for the presence of human IgG and for binding to immobilized Gmd protein by ELISA. Bound antibody was detected using a goat anti-Human IgG antibody coupled to horseradish peroxidase and 3,3', 5, 5' tetramethylbenzidene substrate.

The human:mouse chimeric 4A12 (h4A12) was then tested for its ability to inhibit Gmd enzymatic activity. Mouse IgG1 4A12 and its chimeric form, h4A12, were incubated at the indicated concentrations with Gmd in the presence of heat-killed M. luteus, a substrate for Gmd activity. After incubation at 37° C. for 60 minutes, the degree of cell lysis was measured by comparing the light scattering at 490 nm compared to that at t=0. Percent inhibition was calculated as $100*(1-(\Delta_{60}A_{490}\text{ inhibitor}/\Delta_{60}A_{490}\text{ no inhibitor control}))$. Although the mouse 4A12 monoclonal antibody showed a nearly three-fold difference in the minimum concentration able to achieve ~100% inhibition of Gmd activity, the data confirms that both forms of the antibody are able to completely inhibit Gmd.

Example 10

Passive Vaccine Containing Anti-Gmd mAb 4A12 Inhibits Staphylococcus aureus In Vivo Following Orthopedic Implant in Mouse OM Model The OM model with trans-tibial pin (see Examples 1 and 6) is underway, and will be used to assess the ability of candidate mAb 4A12 to inhibit S. aureus growth in vivo. Briefly, five week old female BALB/cJ mice will receive an intraperitoneal injection of saline (n=10) or 1 mg of purified 4A12 anti-Gmd antibody (n=5) in 0.25 ml saline 3 days prior to surgery. At surgery, the mice will receive a transtibial implant containing 500,000 CFU of Xen29 *S. aureus*. The mice will be imaged to assess bioluminescence on days 0, 3, 5, 7, 10 or 11, and 14, and images with the BLI heat map from a representative animal in each group will be examined.

Based on the early success of this experiment, it is expected that the humanized 4A12 antibody, or Ig class variants thereof, can be utilized alone or in combination with one or more humanized versions of antibodies 1C11, 1E12, 2D11, 3A8 and 3H6 in a phase I clinical trial in elderly patients (>65 yrs) undergoing primary total joint replacement.

Example 11

Anti-Glucosaminidase Antibodies as a Biomarker of Protective Immunity Against *Staphylococcus aureus* in Patients with Orthopaedic Infections Although there are excellent serum-based diagnostic tests to assess the presence of infection (i.e. C-reactive protein; CRP), there are no tests to assay host immunity to *S. aureus*. To test the hypothesis that anti-Gmd antibodies are a serum biomarker of protective immunity, assays were developed to quantify physical and neutralizing titers in sera from infected and non-infected mice, and orthopaedic patients with and without *S. aureus* infections.

A recombinant His-Gmd protein was generated in *E. coli* and purified as the analyte for the anti-Gmd ELISA for physical titer. This ELISA was able to detect anti-Gmd antibodies in the range of 1 ng/ml to 1 µg/ml. The specificity of the ELISA was determined by comparing the titer of anti-Gmd antibodies in sera from naïve mice (n=5) versus mice immunized with His-Gmd protein (n=10). All naïve mice had titers below the detectable limit of 100 which was significantly lower than that of the immunized mice (p<0.05).

The functional titer was determined via an *M. luteus* cell wall digestion assay in which anti-Gmd inhibition of His-Gmd activity was determined by O.D. (FIG. 11A). The box indicates the effective concentration of His-Gmd used in the functional anti-Gmd assay. Its sensitivity was determined as % inhibition of the 3.5 µg/mlHis-Gmd with dilutions of purified 1C11 mAb in which the titer is the inflection point (arrows in FIG. 11B). The specificity of the functional assays was determined with sera dilutions 1:10 from naïve mice, challenged mice and immunized mice described above. (FIG. 11C; p=**0.004). Linear regression analysis demonstrated a significant correlation between the physical and functional titers (% inhibition at a serum dilution of 1:10 in PBS; p-value<0.0002 Pearson's correlation coefficient) as presented in FIG. 11D.

Blood was obtained from 27 patients that had a confirmed *S. aureus* orthopaedic infection and 20 healthy controls immediately before total joint replacement (TJR) surgery. Physical and neutralizing anti-Gmd antibody titers were determine from the sera, and compared to CRP and TNF levels to assess their potential as biomarkers of infection. There were no significant differences in gender, age, BMI, type II diabetes, heart disease, or autoimmunity between patient groups. Both CRP (148.5+/−230.8 vs. 17.8+/−17.2 mg/ml; p<0.02) and TNF (43.0+/−37.5 vs. 20.3+/−11.6 pg/ml; p<0.0001) levels were significantly increased in the sera of the infected patients vs. controls. The significant difference in physical titers (*<0.02), and functional titers (**p<0.0001) between the infection patients and healthy controls are presented in FIGS. 12A and B. A linear regression analysis demonstrated a significant correlation between the physical and functional titers (FIG. 12C; *p-value<0.0001; Pearson's correlation coefficient). Moreover, the receiver-operator characteristics (ROC) curve of anti-Gmd antibodies demonstrated the significance of this test as a serum biomarker of *S. aureus* infection (FIG. 13). In this ROC curve, the physical titers of the uninfected control (open circles) and *S. aureus* infected patient (closed circles) sera were combined and presented with area under the curve (AUC) and significance.

Orthopaedic infections, particularly from methicillin-resistant *S. aureus* (MRSA) have remained a major challenge for the orthopaedic surgeon. As there have been no major clinical advances towards treating these patients over the last 30 years, and the incidence of vancomycin resistant MRSA is on the rise, investigators have been focusing on immunization strategies to prevent and treat these infections. The immune proteome hypothesis posits that effective humoral immunity against *S. aureus* requires the development of a constellation of antibodies against antigens expressed on the surface of the bacteria, although the nature and effective serum concentration of these antibodies remains unknown. In this example, evidence is provided that anti-Gmd antibodies in patient sera are a biomarker of *S. aureus* infection. In addition to the above data, clinical outcome of the infected patients will be correlated with anti-Gmd titers to assess its value as a biomarker of immunity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A monoclonal antibody or antigen binding portion thereof that comprises a $V_H$ domain having the amino acid sequence of SEQ ID NO: 2 and a $V_L$ domain having the amino acid sequence of SEQ ID NO: 3.

2. The monoclonal antibody according to claim 1, wherein the monoclonal antibody binds specifically to a *Staphylococcus aureus* glucosaminidase and inhibits in vivo growth of *S. aureus*.

3. The monoclonal antibody according to claim 2, wherein the *S. aureus* is methicillin resistant.

4. The monoclonal antibody according to claim 1, wherein the monoclonal antibody or antigen binding portion binds to an epitope wholly or partly within the *Staphylococcus aureus* glucosaminidase catalytic domain.

5. The monoclonal antibody according to claim 1, wherein the monoclonal antibody binds to a glucosaminidase containing the amino acid sequence of SEQ ID NO: 1.

6. The monoclonal antibody according to claim 1, wherein the monoclonal antibody promotes cell-independent lysis of *S. aureus*.

7. The monoclonal antibody according to claim 1, wherein the monoclonal antibody inhibits activity of a *Staphylococcus aureus* glucosaminidase by at least about 95%.

8. The monoclonal antibody according to claim 2, wherein the in vivo growth inhibition is measured using an animal model implanted with a transtibial implant infected with 500,000 CFU of a bioluminescent *S. aureus*.

9. The monoclonal antibody according to claim 1, wherein the monoclonal antibody is chimeric.

10. The monoclonal antibody antigen binding portion according to claim 1.

11. The monoclonal antibody antigen binding portion according to claim 10, wherein the antigen binding portion comprises a Fab fragment, Fv fragment, or single-chain antibody.

* * * * *